US008372008B2

(12) United States Patent
Katsuyama

(10) Patent No.: US 8,372,008 B2
(45) Date of Patent: Feb. 12, 2013

(54) ULTRASOUND DIAGNOSTIC APPARATUS AND ULTRASOUND DIAGNOSTIC METHOD

(75) Inventor: Kimito Katsuyama, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 690 days.

(21) Appl. No.: 12/585,482

(22) Filed: Sep. 16, 2009

(65) Prior Publication Data

US 2010/0076312 A1  Mar. 25, 2010

(30) Foreign Application Priority Data

Sep. 25, 2008  (JP) .................................. 2008-245519
Mar. 31, 2009  (JP) .................................. 2009-088363

(51) Int. Cl.
*A61B 8/00* (2006.01)

(52) U.S. Cl. ........ 600/439; 600/407; 600/437; 600/441; 600/447; 600/448

(58) Field of Classification Search .................. 600/407, 600/437, 439–448
See application file for complete search history.

(56) References Cited

U.S. PATENT DOCUMENTS

| 2003/0092990 | A1 | 5/2003 | Baba et al. | |
|---|---|---|---|---|
| 2006/0235302 | A1* | 10/2006 | Grossman et al. | ............ 600/443 |
| 2009/0003128 | A1 | 1/2009 | Jeong et al. | |

FOREIGN PATENT DOCUMENTS

| EP | 0256686 A1 | 2/1988 |
|---|---|---|
| EP | 1262148 A1 | 12/2002 |
| JP | 5-95946 | 4/1993 |
| JP | 2001-252276 A | 9/2001 |
| JP | 2003-070788 A | 3/2003 |
| JP | 2009-521980 A | 6/2009 |
| WO | WO 93/17622 | 9/1993 |
| WO | WO 2007/075040 A1 | 7/2007 |

OTHER PUBLICATIONS

Krucker, et al.; Sound Speed Estimation Using Automatic Ultrasound Image Registration; IEEE Transcations on Ultrasonics, Ferroelectrics and Frequency Control; Sep. 2004; vol. 51, No. 9; The Institute of Electrical and Electronics Engineers, Inc.

Linzer, et. al.; Ultrasonic Tissue Characterization; Annual Review of Biophysics and Bioengineering; Jun. 1982; pp. 303-329; vol. 11.

(Continued)

*Primary Examiner* — Brian Casler
*Assistant Examiner* — Joel Lamprecht
(74) *Attorney, Agent, or Firm* — Jean C. Edwards, Esq.; Edwards Neils PLLC

(57) ABSTRACT

An ultrasound diagnostic apparatus includes: an ultrasound probe including a plurality of ultrasound transducers; a device for determining optimum sound speed values at a lattice point set in a shallower region than a region of interest (ROI) and in the ROI on the basis of an ultrasound detection signal outputted by the ultrasound probe; a device for arithmetically operating a received wave received from the ROI on the basis of the optimum sound speed value; a device for setting an assumed sound speed in the region of interest, obtaining a received wave received from each lattice point on the basis of the assumed sound speed and the optimum sound speed value at the lattice point, and synthesizing received waves at lattice points to obtain a resultant received wave; and a device for determining a local sound speed value in the ROI on the basis of the received wave and the resultant received wave.

19 Claims, 12 Drawing Sheets

FIG.1

OTHER PUBLICATIONS

Anderson, et. al.; The Direct Estimation of Sound Speed using Pulse-Echo Ultrasound; Journal of the Acoustical Society of America, AIP; Nov. 1998; vol. 104, No. 5; Melville, New York.

Schomberg; An Improved Approach to Reconstructive Ultrasound Tomography; Journal of Physics D: Applied Physics; 1978; pp. L181-L185; vol. 11, No. 15.

* cited by examiner

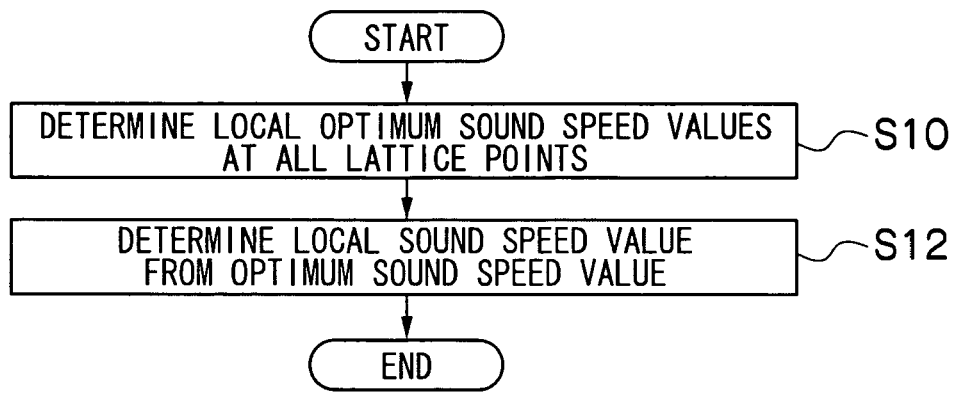
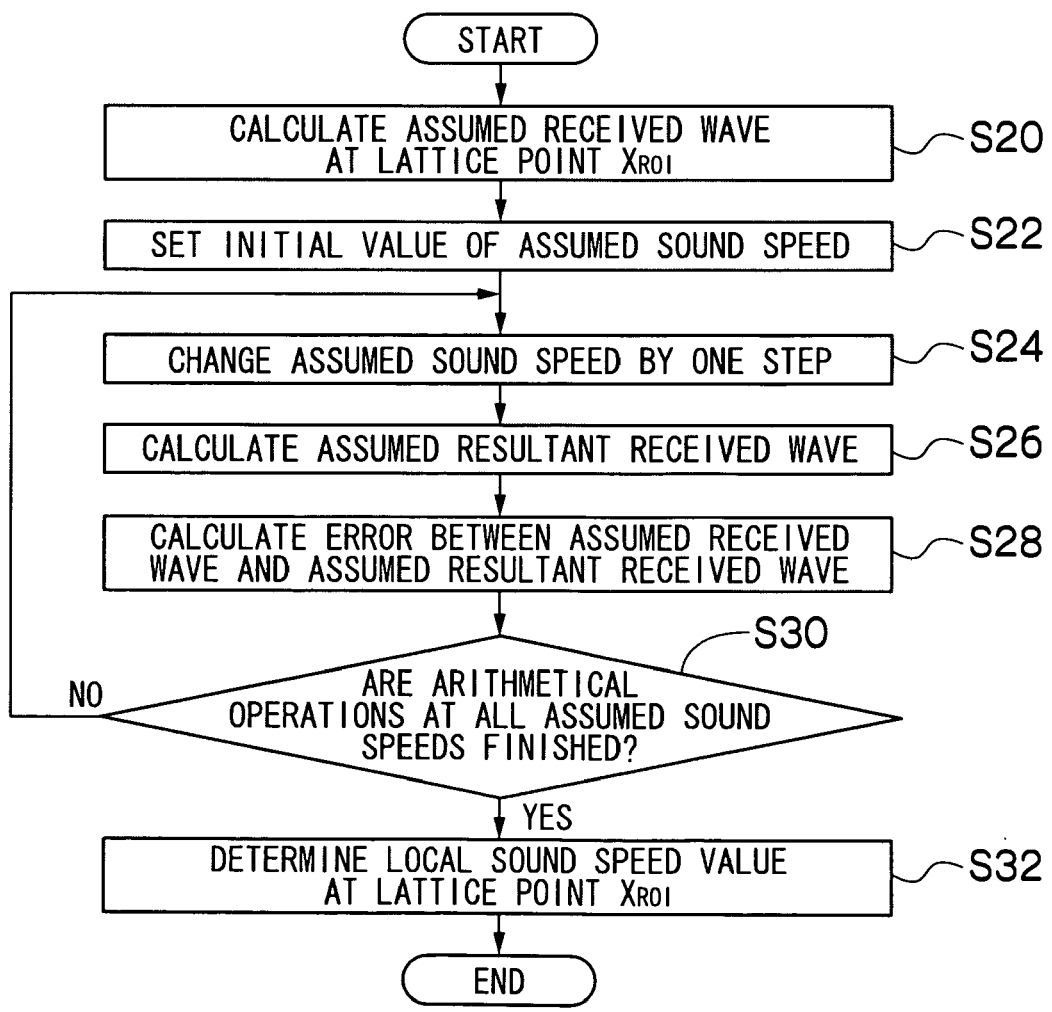

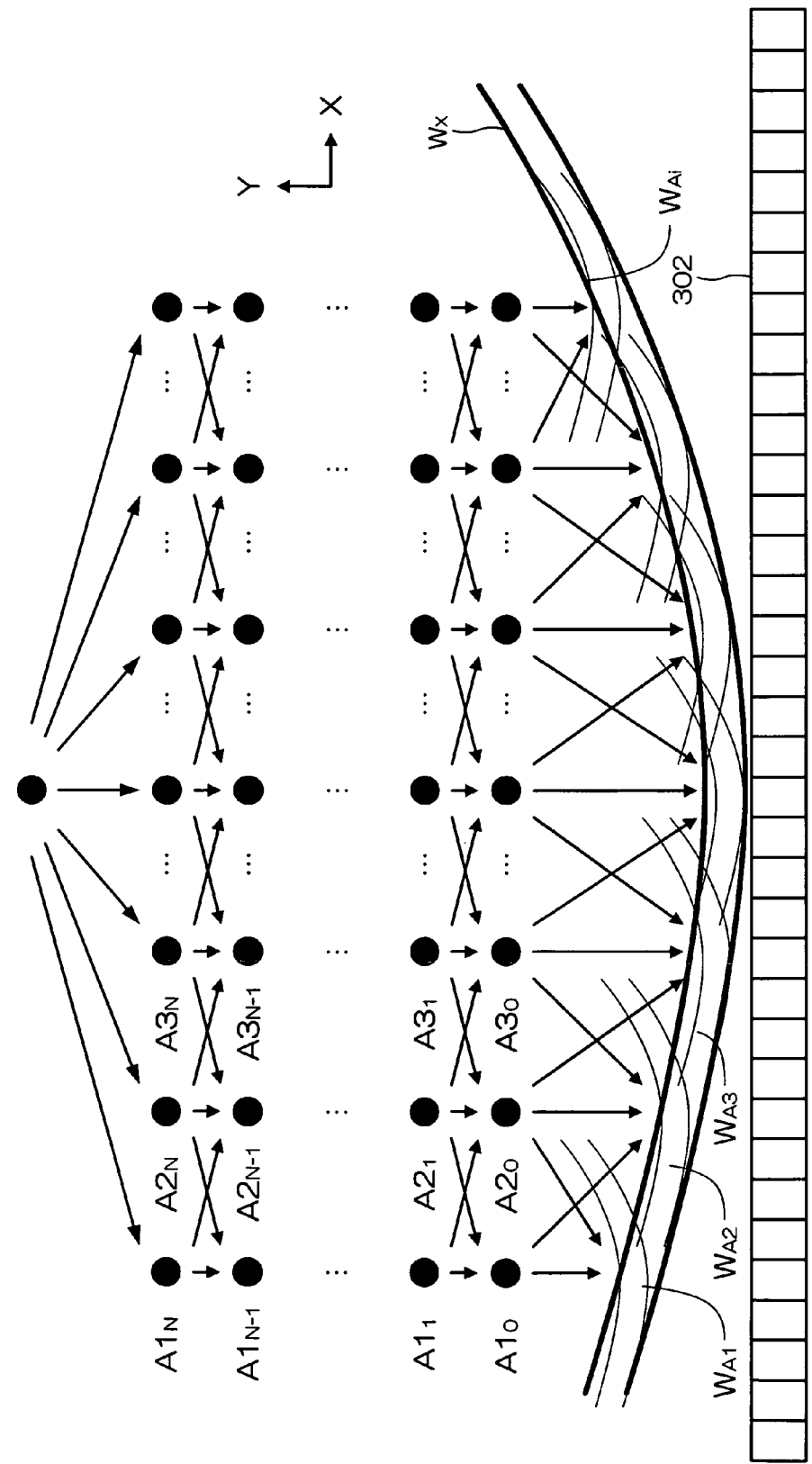

ULTRASOUND DIAGNOSTIC APPARATUS AND ULTRASOUND DIAGNOSTIC METHOD

CROSS-REFERENCE TO RELATED APPLICATIONS

The present application claims priority from Japanese Patent Application No. 2008-245519, filed Sep. 25, 2008, and from Japanese Patent Application No. 2009-088363, filed Mar. 31, 2009, the contents of all of which are herein incorporated by reference in their entirety.

BACKGROUND OF THE INVENTION

1. Field of the Invention

The present invention relates to an ultrasound diagnostic apparatus and an ultrasound diagnostic method, and more particularly to an ultrasound diagnostic apparatus and an ultrasound diagnostic method for taking an ultrasound image of a subject using ultrasound and displaying the ultrasound image.

2. Description of the Related Art

Conventionally, attempts have been made to measure a sound speed value in a part (a region to be diagnosed) in a subject (hereinafter referred to as a local sound speed value) using ultrasound. For example, proposed methods include a method of arranging two transducers for transmitting and receiving to face each other and obtaining a sound speed value in a subject based on a distance between the transducers and a propagation time of ultrasound, and a method of using two pairs of transducers arranged at a predetermined interval as the transducers for transmitting and receiving respectively and obtaining a propagation speed based on a propagation time of ultrasound between the transducers, wave transmitting angles and wave receiving angles, and the interval between the transducers of each pair.

Japanese Patent Application Laid-Open No. 5-95946 discloses a measurement method of a local sound speed value described below. In Japanese Patent Application Laid-Open No. 5-95946, a wave transmitting transducer transmits ultrasound into a subject while changing an emission angle, a wave receiving transducer receives the ultrasound while changing an incident angle, and times elapsing between transmitting and receiving of the ultrasound are all stored in a memory. Then, assumed sound speed distribution is set, and a time elapsing between transmitting and receiving of the ultrasound for each emission angle and each incident angle is calculated on the basis of the sound speed distribution. Then, the assumed sound speed distribution is corrected so as to minimize a difference between a calculated value and an actual measured value of the time, and a sound speed value in the subject is obtained from sound speed distribution obtained finally.

SUMMARY OF THE INVENTION

A sound speed value V in a subject OBJ1 including a medium with a constant sound speed value can be calculated as described below. As shown in FIG. 14A, a time T elapsing between a time ultrasound is reflected at a reflection point (region) $X1_{ROI}$ and a time the ultrasound is received by an element $302A_0$ located immediately below the reflection point $X1_{ROI}$ is T=L/V, where L is a distance between the reflection point $X1_{ROI}$ in the subject OBJ1 and an ultrasound probe 300A. When T+ΔT is a time elapsing between a time the ultrasound is reflected at the reflection point $X1_{ROI}$ and a time the ultrasound is received by an element $302A_i$ located at a distance X from the element $302A_0$ in an X direction (an arrangement direction of elements 302A), a delay time ΔT between the element $302A_0$ and the element $302A_i$ is expressed by the following expression (1):

$$\Delta T = \Delta L/V \text{ (where } \Delta L = \sqrt{L^2 + X^2} - L) \tag{1}$$

Thus, time [2T, 2T+ΔT] elapsing between a time the ultrasound is transmitted and reflected at the reflection point $X1_{ROI}$ the time T later and a time the ultrasound is received by the elements can be measured to uniquely obtain the distance L between the ultrasound probe 300A and the reflection point $X1_{ROI}$ and the speed V.

When the ultrasound from the reflection point $X1_{ROI}$ can be clearly identified, L and V can be determined from the times measured at two different elements having a known positional relationship. However, ultrasound detection signals output from the elements 302A are generally generated by interference of signals from countless reflection points, and it is difficult to identify a signal from a specific reflection point. Thus, actually, the distance L to the reflection point $X1_{ROI}$ the delay time ΔT, and the sound speed value V are uniquely obtained based on a space frequency, sharpness, and contrast of a reconstructed image in a region of interest near the reflection point $X1_{ROI}$.

As described above, when the sound speed in the subject is constant, the sound speed value can be obtained, while when the sound speed in the subject is not constant as in a subject OBJ2 shown in FIG. 14B, it is difficult to obtain a distance L between the ultrasound probe 300A and a reflection point (region) $X2_{ROI}$ and sound speed values V and V' by the above described method.

The present invention is achieved in view of these circumstances, and has an object to provide an ultrasound diagnostic apparatus and an ultrasound diagnostic method which enable to calculate a sound speed value (local sound speed value) in any region to be diagnosed in a subject with high accuracy.

To solve the above described problems, an ultrasound diagnostic apparatus of a first aspect of the present invention includes: an ultrasound probe including a plurality of ultrasound transducers for transmitting ultrasound to a subject and receiving the ultrasound reflected by the subject to output an ultrasound detection signal; an optimum sound speed value determination device for determining optimum sound speed values at a lattice point set in a shallower region than a region of interest in the subject and in the region of interest on the basis of the ultrasound detection signal; a first arithmetical operation device for arithmetically operating a received wave received from the region of interest when the ultrasound is transmitted to the region of interest on the basis of the optimum sound speed value in the region of interest; a second arithmetical operation device for setting an assumed sound speed in the region of interest, obtaining a received wave received from each lattice point when the ultrasound is transmitted to the region of interest on the basis of the assumed sound speed and the optimum sound speed value at the lattice point, and synthesizing received waves at lattice points to obtain a resultant received wave; and a local sound speed value determination device for making a determination of a local sound speed value in the region of interest on the basis of the received wave and the resultant received wave.

According to the first aspect, the local sound speed value in the subject can be determined with high accuracy using an amplitude image obtained in generation of a B (Brightness) mode image, RF (Radio Frequency) data, or data on the received waves received by the ultrasound transducer elements. The local sound speed value obtained as described above can be used to detect a lesion in the subject with higher accuracy. In the first aspect, a configuration exclusively for transmitting ultrasound and a configuration exclusively for receiving ultrasound are not required to be arranged separately, in order to measure the local sound speed value.

The ultrasound diagnostic apparatus of a second aspect of the present invention is such that the local sound speed value determination device determines the assumed sound speed used for arithmetical operation of a received wave at which a delta between the received wave and the resultant received wave is minimized, as a local sound speed value in the region of interest, in the first aspect.

An ultrasound diagnostic apparatus of a third aspect of the present invention includes: an ultrasound probe including a plurality of ultrasound transducers for transmitting ultrasound to a subject and receiving the ultrasound reflected by the subject to output an ultrasound detection signal; an optimum sound speed value determination device for determining an optimum sound speed value in a region between a plurality of lattice points set in a shallower region than a region of interest in the subject and the ultrasound probe on the basis of the ultrasound detection signal; a resultant received wave obtaining device for obtaining received waves received from the plurality of lattice points, and synthesizing the obtained received waves to obtain a first resultant received wave; an arithmetical operation device for setting an assumed sound speed in the region of interest, tracing an acoustic ray of ultrasound transmitted from the ultrasound probe to the region of interest on the basis of the assumed sound speed and optimum sound speed values at the plurality of lattice points, obtaining received waves reflected at the region of interest and reaching the plurality of ultrasound transducers through the plurality of lattice points, and synthesizing the obtained received waves to obtain a second resultant received wave; and a local sound speed value determination device for making a determination of a local sound speed value in the region of interest on the basis of the first and the second resultant received waves.

According to the third aspect, the acoustic ray tracing of the ultrasound reflected at the region of interest in the subject is performed, and the local sound speed value in the region of interest is determined using the received waves directly reaching the ultrasound transducers (elements) of the ultrasound probe, thereby allowing the local sound speed value to be accurately calculated with fewer processes.

The ultrasound diagnostic apparatus of a fourth aspect of the present invention is such that the local sound speed value determination device determines an assumed sound speed used for arithmetical operation of a received wave at which a delta between the first resultant received wave and the second resultant received wave is minimized, as a local sound speed value in the region of interest, in the third aspect.

An ultrasound diagnostic apparatus of a fifth aspect of the present invention includes: an ultrasound probe including a plurality of ultrasound transducers for transmitting ultrasound to a subject and receiving the ultrasound reflected by the subject to output an ultrasound detection signal; an arithmetical operation device for setting an assumed sound speed in a certain region of interest in the subject, obtaining received waves received from a plurality of lattice points set in a shallower region than the region of interest when ultrasound is transmitted from the ultrasound probe to the region of interest on the basis of the assumed sound speed, and synthesizing the received waves from the lattice points to obtain a resultant received wave; a sound speed determination index arithmetical operation device for obtaining a delay from the received waves from the lattice points to generate an image in the region of interest on the basis of the delay, and obtaining a sound speed determination index on the basis of the image; and a local sound speed value determination device for making a determination of a local sound speed value in the region of interest on the basis of the sound speed determination index, and repeating the determination of the local sound speed value in order from a lattice point in a shallow region to determine the local sound speed value in the subject.

According to the fifth aspect, the local sound speed value is determined in order from a shallow layer in the subject, thereby allowing the local sound speed value in the subject to be determined with high accuracy.

The ultrasound diagnostic apparatus of a sixth aspect of the present invention is such that the sound speed determination index arithmetical operation device obtains the sound speed determination index on the basis of at least one of contrast of the image, a space frequency of the image in a scanning direction, and dispersion of the space frequency, in the fifth aspect.

An ultrasound diagnostic apparatus of a seventh aspect of the present invention includes: an ultrasound probe including a plurality of ultrasound transducers for transmitting ultrasound to a subject and receiving the ultrasound reflected by the subject to output an ultrasound detection signal; an arithmetical operation device for setting an assumed sound speed in a certain region of interest in the subject, tracing an acoustic ray of the ultrasound transmitted from the ultrasound probe to the region of interest, and obtaining received waves reflected at the region of interest and reaching the plurality of ultrasound transducers through the plurality of lattice points set in a shallower region than the region of interest on the basis of the assumed sound speed; a sound speed determination index arithmetical operation device for obtaining a delay from the received waves from the plurality of lattice points to generate an image in the region of interest on the basis of the delay, and obtaining a sound speed determination index on the basis of the image; and a local sound speed value determination device for making a determination of a local sound speed value in the region of interest on the basis of the sound speed determination index, and repeating the determination of the local sound speed value in order from a lattice point in a shallow region to determine the local sound speed value in the subject.

According to the seventh aspect, acoustic ray tracing is repeatedly conducted in order from the shallow layer in the subject to determine the local sound speed value, thereby allowing the local sound speed value in the subject to be determined with high accuracy.

The ultrasound diagnostic apparatus of an eighth aspect of the present invention further includes a lattice point setting device for setting a lattice point on a boundary between regions with a substantially uniform sound speed in the subject, in any one of the first to seventh aspects.

The ultrasound diagnostic apparatus of a ninth aspect of the present invention further includes an amplitude image generation device (100, 502) for performing at least one of a transmitting focus process and a receiving focus process on the basis of the determination result of the local sound speed value in the subject to generate an amplitude image indicating an amplitude of the received wave with brightness of a point, in any one of the first to eighth aspects.

The ultrasound diagnostic apparatus of a tenth aspect of the present invention further includes a display device for displaying the determination result of the local sound speed value, in any one of the first to eighth aspects.

The ultrasound diagnostic apparatus of an eleventh aspect of the present invention further includes an amplitude image generation device for generating an amplitude image indicating an amplitude of the received wave with brightness of a point on the basis of the ultrasound detection signal, wherein the display device displays the determination result of the local sound speed value so as to be superimposed on the amplitude image or placed with the amplitude image side by side, in the tenth aspect.

The ultrasound diagnostic apparatus of a twelfth aspect of the present invention further includes an amplitude image generation device for generating an amplitude image indicating an amplitude of the ultrasonic echo with brightness of a point on the basis of the ultrasound detection signal, wherein the display device displays the determination result of the local sound speed value by changing brightness or color of the amplitude image, in the tenth aspect.

The ultrasound diagnostic apparatus of a thirteenth aspect of the present invention further includes a display mode switching device for switching a display mode between a first display mode in which the amplitude image is displayed alone and a second display mode in which the determination result of the local sound speed value in the subject is displayed, in the eleventh or twelfth aspect.

According to the tenth to thirteenth aspects, a device for an operator to observe the determination result of the local sound speed value can be provided in addition to the above described advantages.

An ultrasound diagnostic method of a fourteenth aspect of the present invention includes: an optimum sound speed value determination step of determining optimum sound speed values at a lattice point set in a shallower region than a region of interest in a subject and in the region of interest on the basis of an ultrasound detection signal obtained by an ultrasound probe, the ultrasound probe including a plurality of ultrasound transducers for transmitting ultrasound to the subject and receiving the ultrasound reflected by the subject to output the ultrasound detection signal; a first arithmetical operation step of arithmetically operating a received wave received from the region of interest when the ultrasound is transmitted to the region of interest on the basis of the optimum sound speed value in the region of interest; a second arithmetical operation step of setting an assumed sound speed in the region of interest, obtaining a received wave received from each lattice point when the ultrasound is transmitted to the region of interest on the basis of the assumed sound speed and the optimum sound speed value at the lattice point, and synthesizing received waves at lattice points to obtain a resultant received wave; and a local sound speed value determination step of making a determination of a local sound speed value in the region of interest on the basis of the received wave and the resultant received wave.

The ultrasound diagnostic method of a fifteenth aspect of the present invention is such that the assumed sound speed used for arithmetical operation of a received wave at which a delta between the received wave and the resultant received wave is minimized is determined as a local sound speed value in the region of interest in the local sound speed value determination step in the fourteenth aspect.

An ultrasound diagnostic method of a sixteenth aspect of the present invention includes: an optimum sound speed value determination step of determining an optimum sound speed value in a region between a plurality of lattice points set in a shallower region than a region of interest in a subject and an ultrasound probe on the basis of an ultrasound detection signal obtained by the ultrasound probe, the ultrasound probe including a plurality of ultrasound transducers for transmitting ultrasound to the subject and receiving the ultrasound reflected by the subject to output the ultrasound detection signal; a resultant received wave obtaining step of obtaining received waves received from the plurality of lattice points, and synthesizing the obtained received waves to obtain a first resultant received wave; an arithmetical operation step of setting an assumed sound speed in the region of interest, tracing an acoustic ray of ultrasound transmitted from the ultrasound probe to the region of interest on the basis of the assumed sound speed and optimum sound speed values at the plurality of lattice points, obtaining received waves reflected at the region of interest and reaching the plurality of ultrasound transducers through the plurality of lattice points, and synthesizing the obtained received waves to obtain a second resultant received wave; and a local sound speed value determination step of making a determination of a local sound speed value in the region of interest on the basis of the first and the second resultant received waves.

The ultrasound diagnostic method of a seventeenth aspect of the present invention is such that the assumed sound speed used for arithmetical operation of a received wave at which a delta between the first resultant received wave and the second resultant received wave is minimized is determined as a local sound speed value in the region of interest in the local sound speed value determination step in the sixteenth aspect.

An ultrasound diagnostic method of an eighteenth aspect of the present invention includes: an arithmetical operation step of setting an assumed sound speed in a certain region of interest in a subject, obtaining received waves received from a plurality of lattice points set in a shallower region than the region of interest when ultrasound is transmitted from an ultrasound probe to the region of interest on the basis of the assumed sound speed, and synthesizing the received waves from the lattice points to obtain a resultant received wave; a sound speed determination index arithmetical operation step of obtaining a delay from the received waves from the lattice points to generate an image in the region of interest on the basis of the delay, and obtaining a sound speed determination index on the basis of the image; and a local sound speed value determination step of making a determination of the local sound speed value in the region of interest on the basis of the sound speed determination index, and repeating the determination of the local sound speed value in order from a lattice point in a shallow region to determine the local sound speed value in the subject.

The ultrasound diagnostic method of a nineteenth aspect of the present invention is such that the sound speed determination index is obtained on the basis of at least one of contrast of the image, a space frequency of the image in a scanning direction, and dispersion of the space frequency in the sound speed determination index arithmetical operation step in the eighteenth aspect.

An ultrasound diagnostic method of a twentieth aspect of the present invention includes: an arithmetical operation step of setting an assumed sound speed in a certain region of interest in a subject, tracing an acoustic ray of ultrasound transmitted from a ultrasound probe to the region of interest, the ultrasound probe including a plurality of ultrasound transducers for transmitting ultrasound to the subject and receiving the ultrasound reflected by the subject to output an ultrasound detection signal, and obtaining received waves reflected at the region of interest and reaching the plurality of ultrasound transducers through the plurality of lattice points set in a shallower region than the region of interest on the basis of the assumed sound speed; a sound speed determination index arithmetical operation step of obtaining a delay from the received waves from the plurality of lattice points to generate an image in the region of interest on the basis of the delay, and obtaining a sound speed determination index on the basis of the image; and a local sound speed value determination step of making a determination of the local sound speed value in the region of interest on the basis of the sound speed determination index, and repeating the determination of the local sound speed value in order from a lattice point in a shallow region to determine the local sound speed value in the subject.

The ultrasound diagnostic method of a twenty-first aspect of the present invention further includes a lattice point setting step of setting a lattice point on a boundary between regions with a substantially uniform sound speed in the subject, in any one of the fourteenth to twentieth aspects.

The ultrasound diagnostic method of a twenty-second aspect of the present invention further includes an amplitude image generation step of performing at least one of a transmitting focus process and a receiving focus process on the basis of a determination result of the local sound speed value in the subject to generate an amplitude image indicating an amplitude of the received wave with brightness of a point, in any one of the fourteenth to twenty-first aspects.

The ultrasound diagnostic method of a twenty-third aspect of the present invention further includes a display step of displaying the determination result of the local sound speed value on a display device, in any one of the fourteenth to twenty-first aspects.

The ultrasound diagnostic method of a twenty-fourth aspect of the present invention further includes: an amplitude image generation step of generating an amplitude image indicating an amplitude of the received wave with brightness of a point on the basis of the ultrasound detection signal; and a step of displaying the determination result of the local sound speed value on the display device so as to be superimposed on the amplitude image or placed with the amplitude image side by side, in the twenty-third aspects.

The ultrasound diagnostic method of a twenty-fifth aspect of the present invention further includes: an amplitude image generation step of generating an amplitude image indicating an amplitude of the ultrasonic echo with brightness of a point on the basis of the ultrasound detection signal; and a step of displaying the determination result of the local sound speed value on the display device by changing brightness or color of the amplitude image, in the twenty-third aspect.

The ultrasound diagnostic method of a twenty-sixth aspect of the present invention further includes: a display mode switching step of receiving an instruction input from an operator by a display mode switching device to switch a display mode between a first display mode in which the amplitude image is displayed alone and a second display mode in which the determination result of the local sound speed value in the subject is displayed, and switching the display mode, in the twenty-fourth or twenty-fifth aspect.

According to the present invention, the local sound speed value in the subject can be determined with high accuracy using an amplitude image obtained in generation of a B mode image, RF data, or data on the received waves received by the ultrasound transducer elements. The local sound speed value obtained as described above can be used to detect a lesion in the subject with higher accuracy. A configuration exclusively for transmitting ultrasound and a configuration exclusively for receiving ultrasound are not required to be arranged separately, in order to measure the local sound speed value.

BRIEF DESCRIPTION OF THE DRAWINGS

FIG. 3 is a flowchart showing the arithmetical operation process of the local sound speed value according to the first embodiment of the present invention;

FIG. 4 is a flowchart showing the arithmetical operation process of the local sound speed value according to the first embodiment of the present invention;

FIG. 5 schematically shows an arithmetical operation process of a local sound speed value according to a second embodiment of the present invention;

DETAILED DESCRIPTION OF THE PREFERRED EMBODIMENTS

Now, preferred embodiments of an ultrasound diagnostic apparatus and an ultrasound diagnostic method according to the present invention will be described with reference to the accompanying drawings.

First Embodiment

Figure 1:
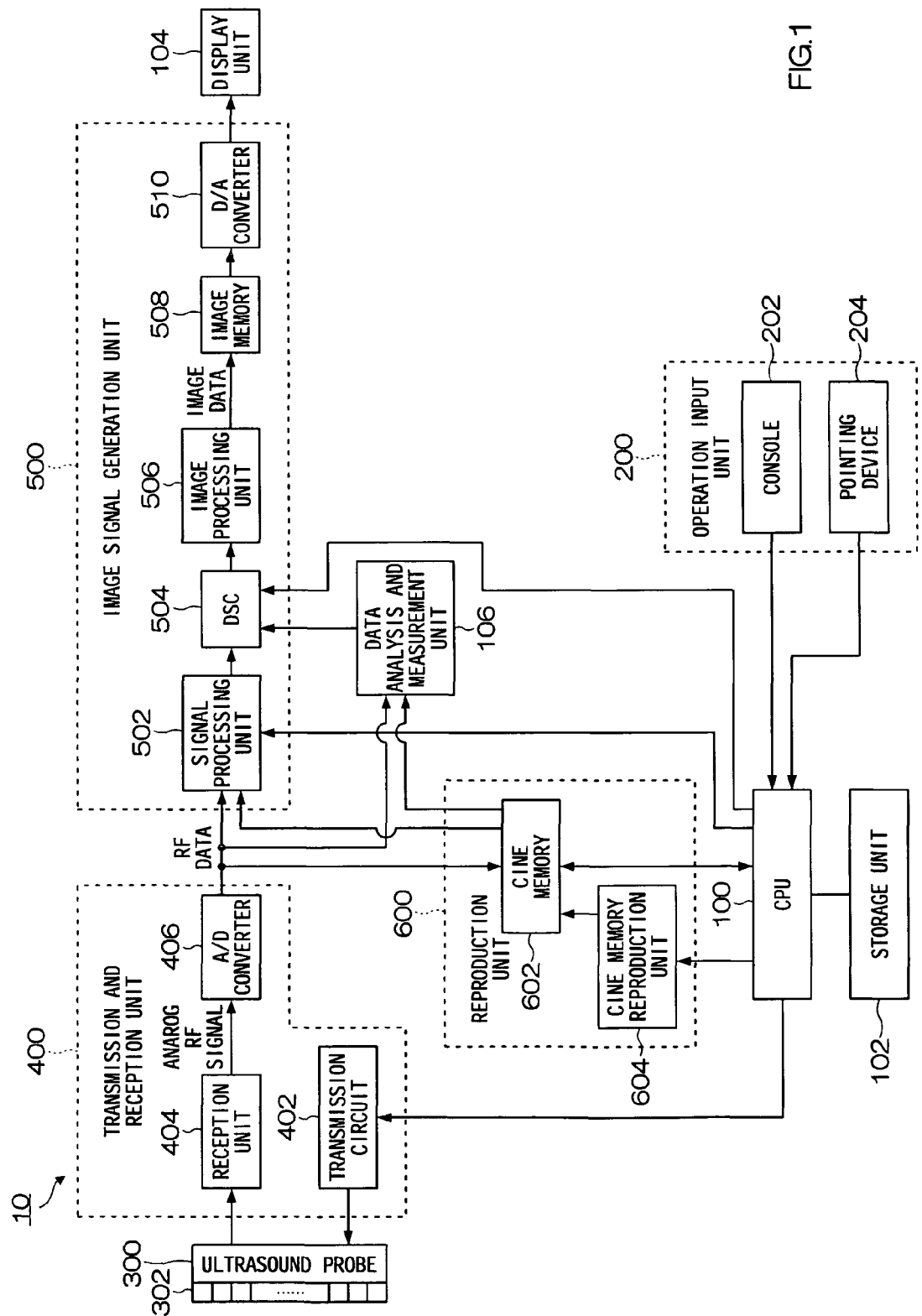
FIG. 1 is a block diagram of an ultrasound diagnostic apparatus according to a first embodiment of the present invention.

FIG. 1 is a block diagram of an ultrasound diagnostic apparatus according to a first embodiment of the present invention.

An ultrasound diagnostic apparatus 10 shown in FIG. 1 is an apparatus that transmits an ultrasound beam from an ultrasound probe 300 to a subject OBJ, receives the ultrasound beam (ultrasonic echo) reflected by the subject OBJ, and generates and displays an ultrasound image from a detection signal of the ultrasonic echo.

A CPU (Central Processing Unit) 100 controls each block in the ultrasound diagnostic apparatus 10 according to an operation input from an operation input unit 200.

The operation input unit 200 is an input device that receives an operation input by an operator, and includes a console 202 and a pointing device 204. The console 202 includes a keyboard that receives an input of character information (for example, patient information), a display mode switch button for switching a display mode between a mode in which an amplitude image (B (Brightness) mode image) is displayed alone and a mode in which a determination result of a local sound speed value is displayed, a freeze button for giving instruction to switch between a live mode and a freeze mode, a cine memory reproduction button for giving instruction to reproduce an image based on data stored in a cine memory, and an analysis and measurement button for giving instruction to analyze and measure an ultrasound image. The pointing device 204 is a device that receives an input of designation of a region on a screen of a display unit 104, for example, a trackball or a mouse. A touch panel may be used as the pointing device 204.

A storage unit 102 is a storage device that stores a control program for the CPU 100 to control each block in the ultrasound diagnostic apparatus 10, for example, a hard disk or a semiconductor memory.

The display unit 104 is, for example, a CRT (Cathode Ray Tube) display or a liquid crystal display, and displays an ultrasound image (moving image and still image) and various setting screens.

The ultrasound probe 300 is a probe to be abutted against the subject OBJ for use, and includes a plurality of ultrasound transducers 302 that constitute a one-dimensional or two-dimensional transducer array. The ultrasound transducer 302 transmits an ultrasound beam to the subject OBJ on the basis of a drive signal applied from a transmission circuit 402, and receives an ultrasonic echo reflected from the subject OBJ to output a detection signal.

The ultrasound transducer 302 includes a transducer including electrodes formed at opposite ends of a piezoelectric material (piezoelectric body). As the piezoelectric body included in the transducer, for example, piezoelectric ceramic such as PZT (Pb (lead) zirconate titanate) or a polymeric piezoelectric element such as PVDF (polyvinylidene difluoride) can be used. When an electric signal is sent to the electrode of the transducer to apply a voltage, the piezoelectric body expands or contracts, and the expansion and contraction of the piezoelectric body causes each transducer to generate ultrasound. For example, when a pulse-like electric signal is sent to the electrode of the transducer, pulse-like ultrasound is generated, and when a continuous wave electric signal is sent to the electrode of the transducer, continuous wave ultrasound is generated. Then, ultrasound generated from each transducer is synthesized to form an ultrasound beam. When each transducer receives ultrasound, the piezoelectric body in each transducer expands and contracts to generate an electric signal. The electric signal generated from each transducer is output to a reception circuit 404 as an ultrasound detection signal.

As the ultrasound transducers 302, a plurality of kinds of elements of different ultrasound conversion types may be used. For example, the transducer including the piezoelectric body is used as an element that transmits ultrasound, and an optical detection type ultrasound transducer may be used as an element that receives ultrasound. The optical detection type ultrasound transducer converts an ultrasound signal into an optical signal for detection, and is, for example, a Fabry-Perot resonator or a fiber Bragg grating.

Next, an ultrasound diagnosis process in the live mode will be described. The live mode is a mode in which an ultrasound image (moving image) obtained by abutting the ultrasound probe 300 against the subject OBJ to transmit and receive ultrasound is displayed, analyzed and measured.

When the ultrasound probe 300 is abutted against the subject OBJ, and ultrasound diagnosis is started by an instruction input from the operation input unit 200, the CPU 100 outputs an control signal to a transmission and reception unit 400, and starts transmitting an ultrasound beam to the subject OBJ and receiving an ultrasonic echo from the subject OBJ. The CPU 100 sets a transmitting direction of the ultrasound beam and a receiving direction of the ultrasonic echo for each ultrasound transducer 302.

Further, the CPU 100 selects a transmission delay pattern according to the transmitting direction of the ultrasound beam, and selects a reception delay pattern according to the receiving direction of the ultrasonic echo. The transmission delay pattern is pattern data of a delay time provided to a drive signal for forming an ultrasound beam in a desired direction by ultrasound transmitted from the plurality of ultrasound transducers 302. The reception delay pattern is pattern data of a delay time provided to a detection signal for extracting an ultrasonic echo from a desired direction by ultrasound received by the plurality of ultrasound transducers 302. The transmission delay pattern and the reception delay pattern are previously stored in the storage unit 102. The CPU 100 selects a transmission delay pattern and a reception delay pattern from the patterns stored in the storage unit 102, and outputs a control signal to the transmission and reception unit 400 to perform control to transmit and receive ultrasound according to the selected transmission delay pattern and reception delay pattern.

The transmission circuit 402 generates a drive signal according to a control signal from the CPU 100, and applies the drive signal to the ultrasound transducer 302. At this time, the transmission circuit 402 delays the drive signal applied to each ultrasound transducer 302 on the basis of the transmission delay pattern selected by the CPU 100. The transmission circuit 402 adjusts (delays) timing of applying the drive signal to each ultrasound transducer 302 so that ultrasound transmitted from the plurality of ultrasound transducers 302 forms an ultrasound beam. The timing of applying the drive signal may be adjusted so that ultrasound transmitted at one time from the plurality of ultrasound transducers 302 reaches the entire imaging region of the subject OBJ.

The reception circuit 404 receives and amplifies an ultrasound detection signal output from each ultrasound transducer 302. As described above, because of different distances between the respective ultrasound transducers 302 and an ultrasound reflection source in the subject OBJ, reflected waves reach the respective ultrasound transducers 302 at different times. The reception circuit 404 includes a delay circuit, and delays each detection signal by an amount corresponding to a difference (delay time) between reaching times of the reflected waves according to a sound speed (hereinafter referred to as an assumed sound speed) set on the basis of the reception delay pattern selected by the CPU 100 or distribution of the sound speed. Then, the reception circuit 404 performs matching addition of the detection signals delayed by the delay time to perform a receiving focus process. When there is a different ultrasound reflection source in a different position from an ultrasound reflection source $X_{ROI}$, an ultrasound detection signal from the different ultrasound reflection source reaches at a different time. Thus, the addition by an addition circuit of the reception circuit 404 causes phases of ultrasound detection signals from different ultrasound reflection sources to cancel each other out. Thus, the received signal from the ultrasound reflection source $X_{ROI}$ is maximized and comes into focus. The receiving focus process forms an acoustic ray signal (hereinafter referred to as an RF (Radio Frequency) signal) with narrowed focus of an ultrasonic echo.

An A/D converter 406 converts an analog RF signal output from the reception circuit 404 into a digital RF signal (hereinafter referred to as RF data). The RF data includes phase information of a received wave (carrier wave). The RF data output from the A/D converter 406 is input to a signal processing unit 502 and a cine memory 602.

The cine memory 602 successively stores the RF data input from the A/D converter 406. The cine memory 602 stores information on a frame rate (for example, a depth of a reflection position of ultrasound, a density of scanning lines, a parameter indicating a width of field of view) input from the CPU 100 in association with the RF data.

The signal processing unit 502 corrects the RF data in attenuation due to a distance according to a depth of a reflection position of ultrasound by STC (Sensitivity Time gain Control), and then performs an envelope detection process of the RF data to generate a B mode image data (image data indicating an amplitude of an ultrasonic echo with brightness of a point).

The B mode image data generated by the signal processing unit 502 is obtained by a different scanning method from a normal television signal scanning method. Thus, a DSC (Digital Scan Converter) 504 converts (raster conversion) the B mode image data into normal image data (for example, image data by the television signal scanning method (NTSC (National Television System Committee in the United States) method)).

An image processing unit 506 performs various necessary image processes (for example, gradation processing) on image data input from the DSC 504.

An image memory 508 stores image data input from the image processing unit 506. A D/A converter 510 converts image data read from the image memory 508 into an analog image signal, and outputs the signal to the display unit 104. Thus, the ultrasound image (moving image) taken by the ultrasound probe 300 is displayed on the display unit 104.

In the embodiment, the detection signal subjected to the receiving focus process in the reception circuit 404 is the RF signal, but a detection signal that is not subjected to the receiving focus process may be an RF signal. In this case, the plurality of ultrasound detection signals output from the plurality of ultrasound transducers 302 are amplified by the reception circuit 404, and the amplified detection signals, that is, the RF signals are A/D converted by the A/D converter 406 to generate RF data. Then, the RF data is supplied to the signal processing unit 502, and stored in the cine memory 602. The receiving focus process is performed by the signal processing unit 502 in digital form.

Next, a cine memory reproduction mode will be described. The cine memory reproduction mode is a mode in which an ultrasound diagnosis image is displayed, analyzed and measured on the basis of the RF data stored in the cine memory 602.

When the cine memory reproduction button on the console 202 is pushed, the CPU 100 switches an operation mode of the ultrasound diagnostic apparatus 10 to the cine memory reproduction mode. In the cine memory reproduction mode, the CPU 100 instructs a cine memory reproduction unit 604 to reproduce RF data designated by an operation input by an operator. The cine memory reproduction unit 604 reads the RF data from the cine memory 602 according to the instruction from the CPU 100, and transmits the read RF data to the signal processing unit 502 in the image signal generation unit 500. The RF data transmitted from the cine memory 602 is subjected to predetermined processes (the same processes as in the live mode) by the signal processing unit 502, the DSC 504, and the image processing unit 506 and converted into image data, and then output via an image memory 508 and the D/A converter 510 to the display unit 104. Thus, the ultrasound image (moving image or still image) based on the RF data stored in the cine memory 602 is displayed on the display unit 104.

When the freeze button on the console 202 is pushed while the ultrasound image (moving image) is displayed in the live mode or the cine memory reproduction mode, the ultrasound image displayed when the freeze button is pushed is displayed as a still image on the display unit 104. This allows the operator to display and observe a still image of a region of interest (ROI).

When the measurement button on the console 202 is pushed, analysis and measurement designated by the operation input by the operator are performed. When the measurement button is pushed in each operation mode, a data analysis and measurement unit 106 obtains RF data before image processing from the A/D converter 406 or the cine memory 602, and uses the RF data to perform analysis and measurement designated by the operator (for example, distortion analysis of a tissue part (diagnosis of hardness), measurement of blood flow, measurement of movement of the tissue part, or measurement of IMT (Intima-Media Thickness) value). Results of analysis and measurement by the data analysis and measurement unit 106 are output to the DSC 504 in the image signal generation unit 500. The DSC 504 inserts the results of the analysis and measurement by the data analysis and measurement unit 106 into image data of the ultrasound image and outputs the data to the display unit 104. Thus, the ultrasound image and the results of the analysis and measurement are displayed on the display unit 104.

When the display mode switching button is pushed, the display mode is switched between a mode in which the B mode image is displayed alone, a mode in which the determination result of the local sound speed value is displayed so as to be superimposed on the B mode image (for example, display with changing color or brightness according to the local sound speed value or display with a line connecting points with the same local sound speed value), and a mode in which the B mode image and the image of the determination result of the local sound speed value are placed side by side. This allows the operator to observe the determination result of the local sound speed value to find, for example, a lesion.

A B mode image obtained by performing at least one of the transmitting focus process and the receiving focus process may be displayed on the display unit 104 on the basis of the determination result of the local sound speed value.

[Arithmetical Operation Process of Local Sound Speed Value]

Figure 2B:
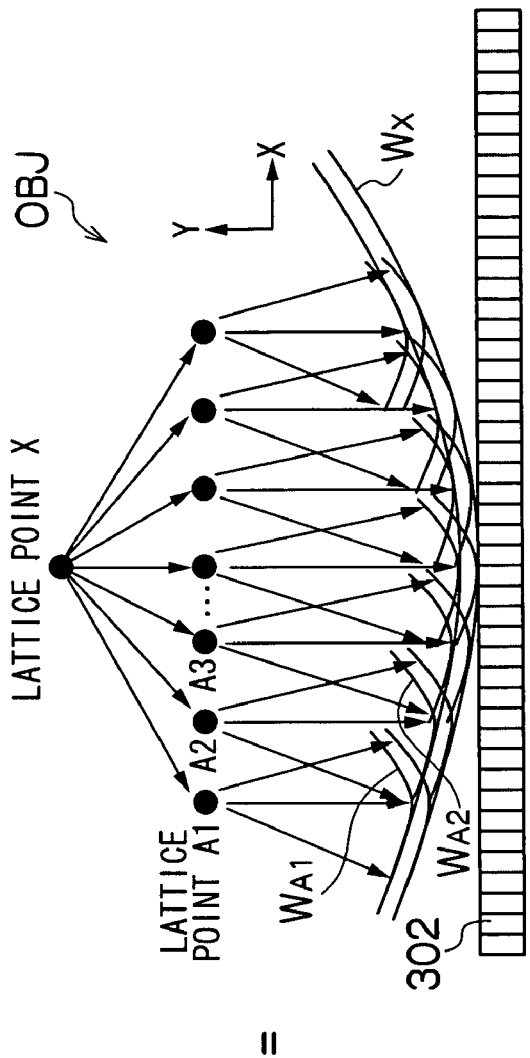
FIGS. 2A and 2B schematically show an arithmetical operation process of a local sound speed value according to the first embodiment of the present invention.
Figure 2A:
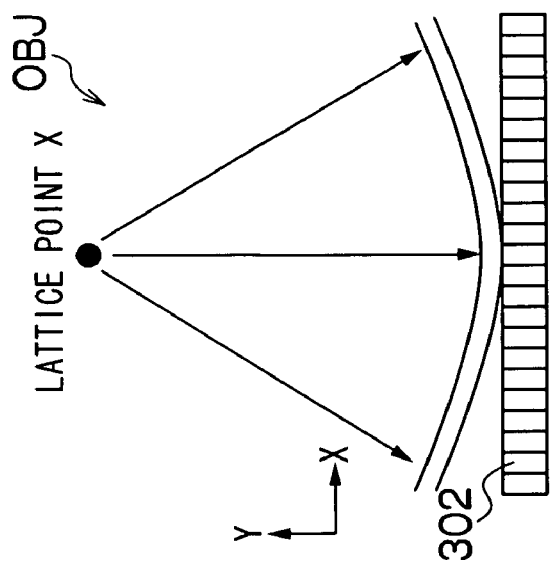

FIGS. 2A and 2B schematically show an arithmetical operation process of the local sound speed value according to the first embodiment of the present invention.

As shown in FIG. 2B, a representative lattice point in the region of interest ROI in the subject OBJ is determined as $X_{ROI}$, and lattice points arranged at regular intervals in X direction in a position shallower than the lattice point $X_{ROI}$ (that is, closer to the ultrasound transducer 302) are determined as $A1, A2, \ldots$, and it is assumed that a sound speed at least between the lattice point $X_{ROI}$ and each of the lattice points $A1, A2, \ldots$ is constant.

In the embodiment, T and delay times $\Delta T$ of received waves ($W_{A1}, W_{A2}, \ldots$, respectively) from the lattice points $A1, A2, \ldots$ are regarded as known, and a local sound speed value at the lattice point $X_{ROI}$ is obtained from a positional relationship between the lattice point $X_{ROI}$ and the lattice points $A1, A2, \ldots$. Specifically, matching is used between an assumed received wave $W_X$ from the lattice point $X_{ROI}$ and a received wave $W_{SUM}$ of an assumed synthesis of the received waves from the lattice points A1, A2, . . . by Huygens' principle.

A range (a region where the lattice points A1, A2, . . . are arranged) and the number of lattice points A1, A2, . . . used in an arithmetical operation for obtaining the local sound speed value at the lattice point $X_{ROI}$ are previously determined. A wide range of lattice points used for the arithmetical operation of the local sound speed value causes a large error in the local sound speed value, and a narrow range causes a large error from the assumed received wave, and thus the range of lattice points is determined by a trade-off therebetween.

The interval between the lattice points A1, A2, . . . in the X direction is determined by a trade-off between resolution and processing time. The interval between the lattice points A1, A2, . . . in the X direction is, for example, nearly 1 mm to 1 cm.

A narrow interval between the lattice points A1, A2, . . . and $X_{ROI}$ in the Y direction causes a large error in error calculation, and a wide interval between the lattice points A1, A2, . . . and $X_{ROI}$ in the Y direction causes a large error in the local sound speed value. The interval between the lattice points A1, A2, . . . and $X_{ROI}$ in the Y direction is determined on the basis of setting of image resolution of an ultrasound image. The interval between the lattice points A1, A2, . . . and $X_{ROI}$ in the Y direction is, for example, nearly 1 cm.

The wide interval between the lattice points A1, A2, . . . makes difficult an arithmetical operation (described later) of a resultant wave, and thus fine lattice points may be generated by interpolation.

Now, the arithmetical operation process of the local sound speed value according to the embodiment will be described with reference to flowcharts in FIGS. 3 and 4.

In the embodiment, first, as shown in FIG. 3, optimum sound speed values at all lattice points set in the subject OBJ are previously determined (step S10). The optimum sound speed value is a sound speed value with the highest contrast and sharpness of an image, and does not always match the actual local sound speed value at each lattice. As a determination method of the optimum sound speed value in step S10, for example, a method of determining an optimum sound speed value from contrast of the image, a space frequency of the image in a scanning direction, and dispersion of the space frequency (for example, Japanese Patent Application Laid-Open No. 8-317926) may be applied.

Next, a local sound speed value at each lattice point is determined on the basis of the optimum sound speed value at each lattice point (step S12).

A method of determining the local sound speed value on the basis of the optimum sound speed value will be described. First, as shown in FIG. 4, a waveform of an assumed received wave $W_X$ with the lattice point $X_{ROI}$ as a reflection point is calculated on the basis of the optimum sound speed value at the lattice point $X_{ROI}$ (step S20).

Then, an initial value of an assumed sound speed at the lattice point $X_{ROI}$ is set (step S22). Then, the assumed sound speed is changed by one step (step S24), and an assumed resultant received wave $W_{SUM}$ is calculated (step S26). When the local sound speed value at the lattice point $X_{ROI}$ is assumed as V, times that elapses after the ultrasound propagating from the lattice point $X_{ROI}$ before reaching the lattice points A1, A2, . . . are $X_{ROI}$A1/V, $X_{ROI}$A2/V, . . . respectively. The $X_{ROI}$A1, $X_{ROI}$A2, . . . are distances between the lattice points A1, A2, . . . , respectively, and the lattice point $X_{ROI}$. The optimum sound speed values at the lattice points A1, A2, . . . are known by step S10, and thus received waves from the lattice points A1, A2, . . . can be previously obtained. Thus, reflected waves (ultrasonic echo) generated with delays $X_{ROI}$A1/V, $X_{ROI}$A2/V, . . . from the lattice points A1, A2, . . . can be synthesized to obtain the assumed resultant received wave $W_{SUM}$.

Actually, the above described processing is performed on element data (RF signal), and thus times (T1, T2, . . . respectively) that elapses after the ultrasound propagating from the lattice point $X_{ROI}$ before reaching the lattice points A1, A2, . . . are expressed by the following expression (2):

$$T1 = \sqrt{(X_{A1}/V)^2 + (\Delta t/2)^2},$$

$$T2 = \sqrt{(X_{A2}/V)^2 + (\Delta t/2)^2},$$

$$T3 = \qquad (2)$$

where $X_{A1}$, $X_{A2}$, . . . are distances between the lattice points A1, A2, . . . and the lattice point X in the scanning direction (X direction) respectively, and $\Delta t$ is a time interval of the lattice points in the Y direction.

Received waves from the lattice points A1, A2, . . . can be synthesized with a delay obtained by adding, to T1, T2, . . . , a time ($\Delta t/2$) that elapses before the ultrasound arriving at the lattice point $X_{ROI}$ from a lattice point An on the same acoustic ray as the lattice point $X_{ROI}$ (for example, on the same straight line which extends to the ultrasound probe 300 from the lattice point $X_{ROI}$) to obtain the assumed resultant received wave $W_{SUM}$.

When the lattice points are set at regular intervals ($\Delta t$) on a time axis in the Y direction, the lattice points are not always arranged at regular intervals on a space. Thus, when the time that elapses before the ultrasound arriving at each lattice point is calculated, corrected $\Delta t/2$ may replace $\Delta t/2$ in the expression (2). The corrected $\Delta t/2$ is, for example, a value obtained by adding or subtracting, to or from $\Delta t/2$, a value obtained by dividing by V a difference in a depth (distance in the Y direction) of A1, A2, . . . from the lattice point An on the same acoustic ray as the lattice point $X_{ROI}$. The depth of each of the lattice points A1, A2, . . . can be obtained by a known local sound speed at a shallower lattice point than the lattice points A1, A2, . . . .

The assumed resultant received wave $W_{SUM}$ is calculated by actually superimposing predetermined pulse waves ($W_{A1}$, $W_{A2}$, . . . respectively) generated from the lattice points A1, A2, . . . with the delays $X_{ROI}$A1/V, $X_{ROI}$A2/V, . . . respectively.

Next, an error (delta) between the assumed received wave $W_X$ and the assumed resultant received wave $W_{SUM}$ is calculated (step S28). The error between the assumed received wave $W_X$ and the assumed resultant received wave $W_{SUM}$ can be calculated by taking cross-correlation between the waves; delaying the assumed received wave $W_X$ by a delay obtained from the assumed resultant received wave $W_{SUM}$ to perform phase matching addition of the waves; or delaying the assumed resultant received wave $W_{SUM}$ by a delay obtained from the assumed received wave $W_X$ to perform phase matching addition of the waves. To obtain the delay from the assumed received wave $W_X$, a time that elapses after the ultrasound propagating at the sound speed V before reaching each element may be regarded as the delay when the lattice point $X_{ROI}$ is a reflection point. To obtain the delay from the assumed resultant received wave $W_{SUM}$, an equiphase line is extracted from a phase difference between resultant received waves of adjacent elements, and the equiphase line may be regarded as a delay, or a phase difference between maximum (peak) positions of the resultant received waves from the elements may be simply regarded as a delay. A correlation peak position of the resultant received wave from the elements may be regarded as a delay. The error in phase matching addition is obtained from peak to peak of a waveform after matching addition, or a maximum value of an amplitude after envelope detection.

Then, steps S24 to S30 are repeated, and when arithmetical operations at all assumed sound speed values are finished (Yes in step S30), the local sound speed value at the lattice point $X_{ROI}$ is determined (step S32). With strict application of Huygens' principle, the waveform of the assumed resultant received wave $W_{SUM}$ obtained in step S26 is equal to the waveform of the assumed received wave (reflected wave) $W_X$ when the local sound speed value at the lattice point $X_{ROI}$ is assumed as V. In step S32, a value of an assumed sound speed at which the error between the assumed received wave $W_X$ and the assumed resultant received wave $W_{SUM}$ is at minimum is determined as a local sound speed value at the lattice point $X_{ROI}$.

According to the embodiment, the local sound speed value in the subject can be determined with high accuracy by using an amplitude image obtained by generating a B mode image, RF data, or data of the received waves received by the ultrasound transducer elements. The local sound speed value obtained as described above can be used to detect a lesion in the subject with higher accuracy. According to the embodiment, a configuration exclusively for transmitting ultrasound and a configuration exclusively for receiving ultrasound are not required to be arranged separately, in order to measure the local sound speed value.

Instead of the above described method (calculation of the waveform of the assumed resultant received wave, calculation of the error (delta) in waveform between the assumed resultant received wave and the assumed received waveform, and determination of the sound speed), a table may be used with an optimum sound speed at the lattice point $X_{ROI}$ and optimum sound speed values at the lattice points A1, A2, . . . as inputs and a sound speed value at the lattice point $X_{ROI}$ as an output.

Also, multiple times of determination of the local sound speed value may be performed using lattice points with a different interval and in a different range (region).

Second Embodiment

Next, a second embodiment of the present invention will be described. In the descriptions below, descriptions relating to the same configurations as in the first embodiment will be omitted.

Figure 6:
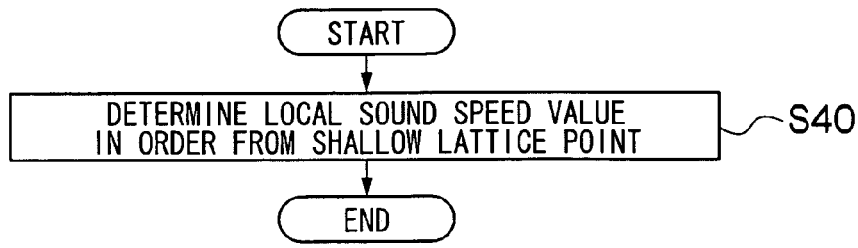
FIG. 6 is a flowchart showing the arithmetical operation process of the local sound speed value according to the second embodiment of the present invention.

As shown in FIGS. 5 and 6, in the embodiment, local sound speed values are determined in order from a lattice point in a shallow layer (in order of $A1_0, A2_0, \ldots, A1_1, A2_1, \ldots, A1_N, A2_N, \ldots$) to determine a local sound speed value at a region of interest (lattice point $X_{ROI}$). It is assumed that a local sound speed value is constant from lattice points ($A1_N, A2_N, \ldots$) in a certain depth to lattice points ($A1_{N-1}, A2_{N-1}, \ldots$) in a one step shallower layer. It is also assumed that a local sound speed value is constant from lattice points ($A1_0, A2_0, \ldots$) in the shallowest layer to an ultrasound probe 300

Now, an arithmetical operation process of a local sound speed value according to the embodiment will be described in detail with reference to a flowchart in FIG. 7.

Figure 7:
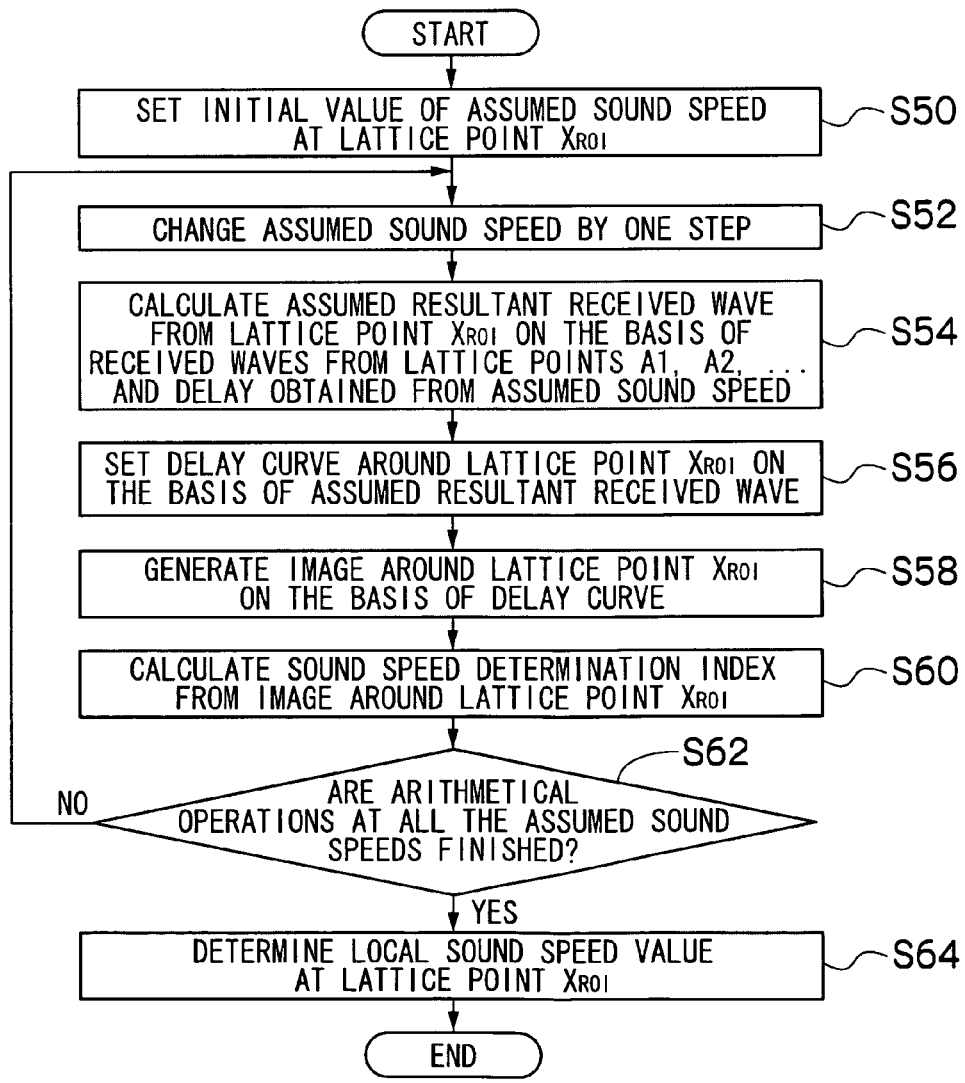
FIG. 7 is a flowchart showing the arithmetical operation process of the local sound speed value according to the second embodiment of the present invention.

In the embodiment, the arithmetical operation process of the local sound speed value shown in FIG. 7 is performed in order from a lattice point in a shallow layer. In the arithmetical operation of the local sound speed value, to determine a sound speed value of a lattice point in a certain depth, a received wave from a lattice point in a shallower depth than the certain depth is required. Thus, to determine local sound speed values at lattice points ($A1_N, A2_N, \ldots$) in a depth N, received waves from all lattice points ($A1_{N-1}, A2_{N-1}, \ldots$) in a depth (N−1) are held in a memory (storage unit 102). After the processing of all lattice points in the depth N is finished, the received waves in the depth (N−1) are abandoned, and received waves from all lattice points in the depth N are held instead.

The received waves and the local sound speed values at the lattice points ($A1_0, A2_0, \ldots$) in the shallowest layer can be obtained by a simple method. The received waves and the local sound speed values at the lattice points ($A1_1, A2_1, \ldots$) in depth "1" are determined by the arithmetical operation process by using the received waves and the local sound speed values at the lattice points ($A1_0, A2_0, \ldots$) in depth "0". By repeating the process, the local sound speed values at the lattice points ($A1_2, A2_2, \ldots A1_N, A2_N, \ldots$) in depth "2", . . . , "N" and the lattice point $X_{ROI}$ are determined by using the received waves and the local speed values at the lattice points in the shallower depth (i.e. depth "1", . . . , "(N−1)", "N"). In the description below concerning the operation for each depth, the subscripts of the lattice points A1, . . . are omitted, and the lattice point which becomes a target of determining the received wave and the local sound speed value in the operation in each depth is represented as $X_{ROI}$.

A range of lattice points (a region where the lattice points $A1_0, A2_0, \ldots, A1_1, A2_1, \ldots, A1_N, A2_N, \ldots$ are arranged) and an interval between the lattice points in XY directions used in the arithmetical operation of the local sound speed value are previously determined as in the first embodiment. Multiple times of determination of the local sound speed value may be performed using lattice points with a different interval and in a different range.

Next, as shown in FIG. 7, an initial value of an assumed sound speed at a lattice point $X_{ROI}$ is set (step S50). Then, the assumed sound speed is changed by one step (step S52), and an assumed resultant received wave $W_{SUM}$ from the lattice point $X_{ROI}$ is calculated from received waves from the lattice points A1, A2, . . . and a delay obtained from the assumed sound speed (step S54).

Then, a delay curve around the lattice point $X_{ROI}$ is set from the assumed resultant received wave $W_{SUM}$ (step S56). As a method of setting a delay curve from the assumed resultant received wave $W_{SUM}$, for example, a method of extracting an equiphase line of the assumed resultant received wave, a method of extracting a maximum amplitude position, or a method of extracting a correlation peak position may be applied.

The received waves at the lattice points A1, A2, . . . with the delay may be set as delay curves without calculating the assumed resultant received wave $W_{SUM}$ to perform matching addition for all delay curves.

For signals of the lattice points A1, A2, . . . obtained by matching addition with the received waves at the lattice points A1, A2, . . . set as the delay curves, further matching addition may be performed according to delay based on distances between the lattice point $X_{ROI}$ and the lattice points A1, A2, . . . . In the embodiment, the lattice points A1, A2, . . . are regarded as assumed elements, a received signal at each assumed element is obtained as a result of the matching addition of the received wave from each assumed element. Then, assuming that a reflected wave from the lattice point $X_{ROI}$ to each assumed element is a wave propagating an uniform sound speed medium, a receiving time and a delay of the reflected wave are obtained to determine a local sound speed value at the lattice point $X_{ROI}$.

Then, an ultrasound image (B mode image) around the lattice point $X_{ROI}$ is generated on the basis of the delay curve (step S58), and a sound speed determination index is calculated from the image around the lattice point $X_{ROI}$ (step S60). The sound speed determination index is an index for determining a sound speed obtained on the basis of at least one of contrast of the image, a space frequency of the image in a scanning direction, and dispersion of the space frequency. Calculation of the sound speed determination index may be performed after image generation of all assumed sound speeds (after step S62).

Then, steps S52 to S62 are repeated, and when arithmetical operations at all assumed sound speed values are finished (Yes in step S62), the local sound speed value at the lattice point $X_{ROI}$ is determined on the basis of the sound speed determination index (step S64).

According to the embodiment, the local sound speed value is determined in order from the shallow layer in the subject OBJ, thereby allowing the local sound speed value in the subject to be determined with high accuracy.

Third Embodiment

Next, a third embodiment of the present invention will be described. In the descriptions below, descriptions relating to the same configurations as in the first embodiment will be omitted.

Figure 8:
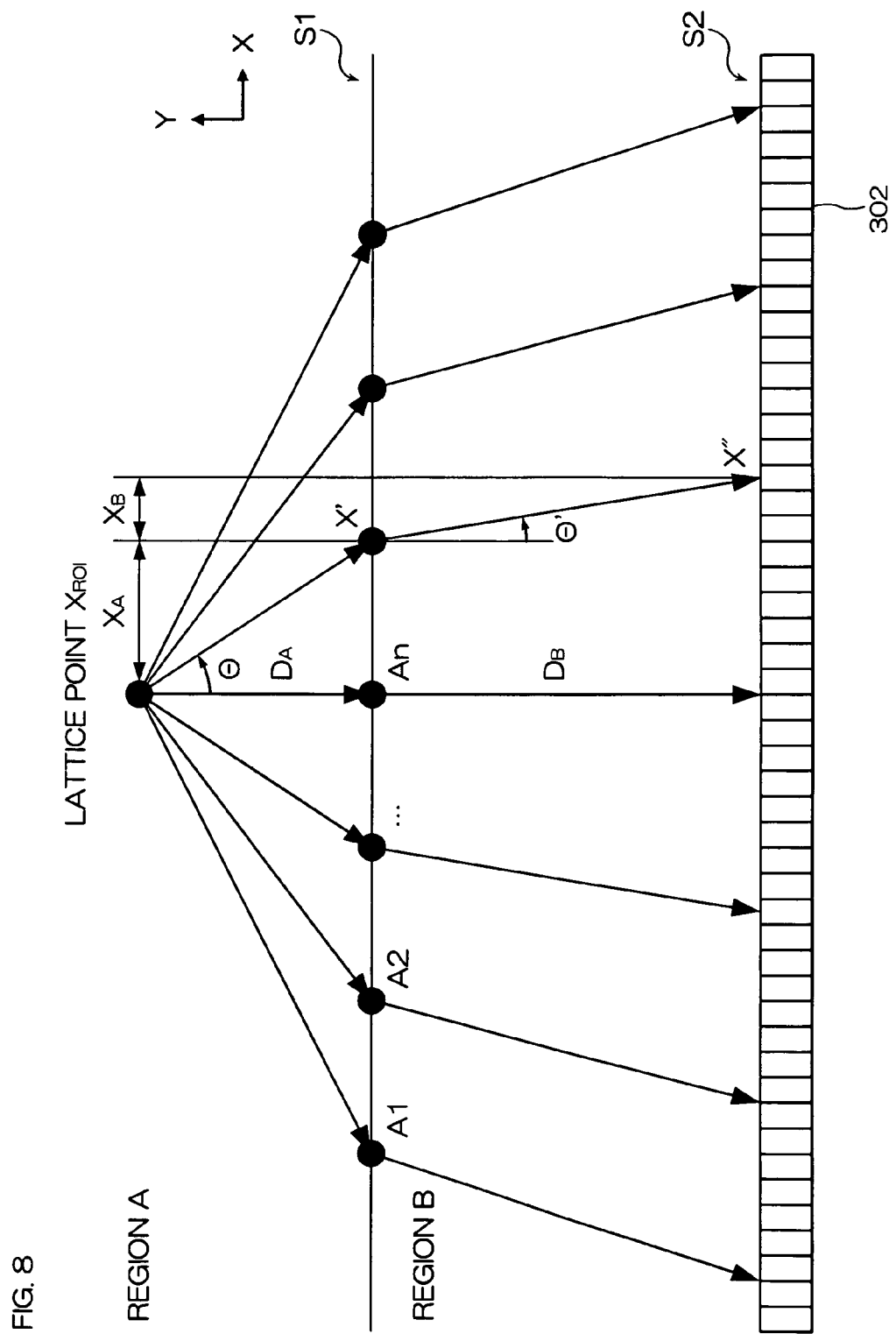
FIG. 8 schematically shows an arithmetical operation procedure of a local sound speed value in a subject according to a third embodiment of the present invention.

FIG. 8 schematically shows an arithmetic operation procedure of a local sound speed value in a subject according to a third embodiment of the present invention.

In the descriptions below, a direction parallel to an element surface S2 on which an ultrasound transducer 302 is placed is an X direction, and a direction perpendicular to the X direction (a depth direction of a subject OBJ) is a Y direction.

As shown in FIG. 8, a representative lattice point in a region of interest ROI in a region A in the subject OBJ is determined as $X_{ROI}$, and lattice points arranged at regular intervals in the X direction in a position shallower than the lattice point $X_{ROI}$ (that is, closer to the ultrasound transducer 302) in the subject OBJ are determined as A1, A2, ..., An, .... The region A is a region between a line (hereinafter referred to as a boundary surface S1) connecting the lattice points A1, A2, ..., An, ... and the lattice point $X_{ROI}$ in the subject OBJ, and a region B is a region between the boundary surface S1 and the element surface S2 of the ultrasound probe 300. It is assumed that sound speeds in the region A and the region B are constant respectively.

In the embodiment, when local optimum sound speeds (environmental sound speeds) in the regions from the lattice points A1, A2, ... to the element surface S2 of the ultrasound probe 300 are substantially the same, received waves from the lattice points A1, A2, ... are the same each other, the received waves are considered to be approximately the same, or the received waves gently change, as shown in FIG. 8, on the basis of a sound speed (assumed sound speed) in the region A between the lattice point $X_{ROI}$ and the lattice points A1, A2, ... and an environmental sound speed in the region B, an acoustic ray refracted at the boundary surface between the regions A and B is traced by Snell's law to obtain a receiving time at each element, instead that the received waves from the lattice points A1, A2, ... are synthesized to generate an assumed received wave and obtain a receiving time at each element.

Figure 9:
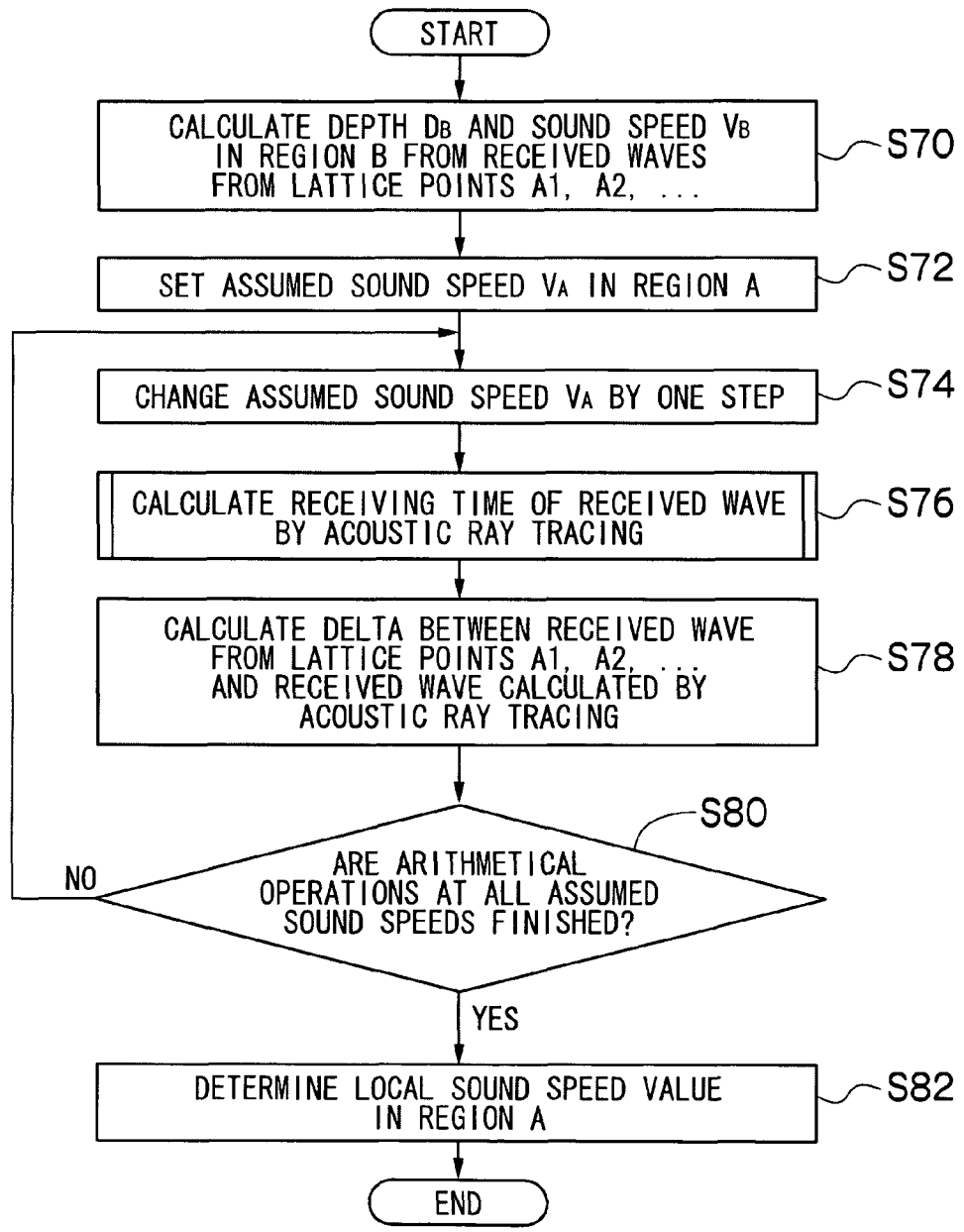
FIG. 9 is a flowchart showing an arithmetical operation process of the local sound speed value according to the third embodiment of the present invention.

FIG. 9 is a flowchart showing an arithmetical operation process of the local sound speed value in the subject according to the third embodiment of the present invention.

First, an optimum sound speed value (environmental sound speed) $V_B$ in the region B is calculated on the basis of received waves received from the lattice points A1, A2, ..., An, ... set in the subject OBJ (step S70). Then, a time (receiving time) $T_B$ for ultrasound transmitted in a +Y direction from the ultrasound transducer 302 to be reflected in a −Y direction at the boundary surface S1 between the regions A and B and return to the ultrasound transducer 302 is measured, and a depth $D_B$ of the region B is calculated based on the environmental sound speed $V_B$ and the receiving time $T_B$ by the following expression (3):

$$D_B = T_B \times V_B / 2 \qquad (3)$$

The optimum sound speed value is a sound speed value with the highest contrast and sharpness of an image, and does not always match the actual local sound speed value at each lattice. As a method of determining an optimum sound speed value in step S70, for example, a method of determination from contrast of the image, a space frequency of the image in a scanning direction, and dispersion of the space frequency (for example, Japanese Patent Application Laid-Open No. 8-317926) may be applied.

Next, an initial value $V_A$ of a local sound speed value (assumed sound speed) in the region A is set (step S72). Then, the assumed sound speed $V_A$ is changed by one step (step S74). Then, a time (receiving time) $T_A$ for ultrasound transmitted in the +Y direction from a lattice point An in line with the lattice point $X_{ROI}$ in the Y direction (on the same X coordinate) to be reflected in the −Y direction at the lattice point $X_{ROI}$ and return to the lattice point An is measured, and a depth $D_A$ of the region A is calculated based on the assumed sound speed $V_A$ and the receiving time $T_A$ by the following expression (4):

$$D_A = T_A \times V_A / 2 \qquad (4)$$

Then, on the basis of the assumed sound speed $V_A$ and the environmental sound speed $V_B$, acoustic ray tracing of the received wave reflected at the lattice point $X_{ROI}$ and reaching the ultrasound transducer 302 is performed, and a receiving time of the received wave is calculated (step S76). Processing of the acoustic ray tracing in step S76 will be described later.

Then, in step S70, an error (delta) between a received wave W1 received from the lattice points A1, A2, ..., An, ... and a received wave W2 calculated by the acoustic ray tracing in step S76 is calculated (step S78). In step S78, the error between the received waves W1 and W2 can be calculated by taking cross-correlation between the waves; delaying the received wave W1 received from the lattice points A1, A2, ..., An, ... by a delay obtained from the received wave W2 calculated by the acoustic ray tracing to perform phase matching addition of the waves; or, conversely, by delaying the received wave W2 calculated by the acoustic ray tracing by the delay obtained from the received wave W1 received from the lattice points A1, A2, ..., An, ... to perform phase matching addition of the waves. To obtain the delay from the received wave W1 received from the lattice points A1, A2, ..., An, ..., and a time that elapses after the ultrasound propagating at the sound speed V before reaching each element may be regarded as a delay when the lattice point $X_{ROI}$ is regarded as a reflection point. To obtain the delay from the received wave W2 calculated by the acoustic ray tracing, an equiphase line is extracted from a phase difference between resultant received waves obtained by synthesizing received waves of adjacent elements, and the equiphase line may be regarded as a delay; or a phase difference between maximum (peak) positions of the resultant received waves of the elements may be regarded as a delay. A correlation peak position of the resultant received wave from the elements may be regarded as a delay. The error in phase matching addition is obtained from peak to peak of a waveform after matching addition or a maximum value of an amplitude after envelope detection.

Then, steps S74 to S80 are repeated, and when arithmetical operations at all assumed sound speed values are finished (Yes in step S80), a local sound speed value at the lattice point $X_{ROI}$ is determined (step S82). In step S82, a value of the assumed sound speed $V_A$ at which a difference in receiving time (absolute value of difference) between the received wave W1 received from the lattice points A1, A2, ..., An, ... in step S70 and the received wave W2 calculated by the acoustic ray tracing in step S76 is at minimum is determined as a local sound speed value at the lattice point $X_{ROI}$.

Now, a calculation process of the receiving time of the received wave by the acoustic ray tracing in step S76 will be described with reference to a flowchart in FIG. 10.

First, an initial value of an emission angle $\Theta$ of ultrasound from the lattice point $X_{ROI}$ is set, and a parameter n is set to n=0 (step S90). Then, the emission angle $\Theta$ is changed by one step and updated to $\Theta = \Theta + \Delta\Theta$ ($\Delta\Theta$: predetermined angle), and the parameter n is updated to n=n+1 (step S92).

Then, a propagation time $T_{AR}$ that elapses after ultrasound emitted from the lattice point $X_{ROI}$ at the updated emission angle $\Theta$ before reaching the boundary surface S1 between the region A and the region B, and a reaching position X' of the ultrasound on the boundary surface S1 is calculated (step S94).

When an X coordinate of the lattice point $X_{ROI}$ is $X_0$, and an X coordinate of a point X' is X', a distance $X_A$ in the X direction between the lattice point $X_{ROI}$ and the point X' is obtained by the following expression (5):

$$X_A = |X' - X_0| = D_A \times \tan\Theta \quad (5)$$

The propagation time $T_{AR}$ that elapses after the ultrasound emitted from the lattice point $X_{ROI}$ before reaching the point X' on the boundary surface S1 is obtained by the following expression (6).

$$T_{AR} = D_A / V_A / \cos\Theta \quad (6)$$

Then, an emission angle $\Theta'$ when the ultrasound emitted from the lattice point $X_{ROI}$ at the emission angle $\Theta$ and reaching the point X' on the boundary surface S1 is emitted from the point X' to the region B is calculated according to Snell's law. Then, an ultrasound propagation time $T_{BR}$ that elapses after the ultrasound emitted from the point X' at the emission angle $\Theta'$ before reaching the element surface S2 of the ultrasound probe 300, and a reaching position X" of the ultrasound on the element surface S2 are calculated (step S96).

The emission angle $\Theta'$ from the point X' is obtained by the following expression (7):

$$\Theta' = \arcsin(V_B \times \sin\Theta / V_A) \quad (7)$$

When an X coordinate of a point X" is X", a distance $X_B$ in the X direction between the point X' and the point X" is obtained by the following expression (8):

$$X_B = |X'' - X'| = D_B \times \tan\Theta' \quad (8)$$

The propagation time $T_{BR}$ that elapses after the ultrasound emitted from the point X' before reaching the point X" on the boundary surface S2 is obtained by the following expression (9):

$$T_{BR} = D_B / V_B / \cos\Theta' \quad (9)$$

Then, a time $T_{SUM} (= T_{AT} + T_{BT} + T_{AR} + T_{BR})$ that elapses after the ultrasound emitted from the element surface S2 to be reflected at the lattice point $X_{ROI}$ before returning to the element surface S2 is calculated, and stored as n-th receiving time data Dn with the reaching position X" of the ultrasound (step S98).

$T_{AT}$ and $T_{BT}$ are transmission times for the ultrasound transmitted in the +Y direction from the ultrasound transducer 302 to propagate through the regions A and B, respectively. The transmission times $T_{AT}$ and $T_{BT}$ are obtained by the following expressions (10) and (11):

$$T_{AT} = T_A / 2, \quad (10)$$

$$T_{BT} = T_B / 2, \quad (11)$$

Then, steps S92 to S100 are repeated, and arithmetical operations at all emission angles $\Theta$ (for example, angles in a range receivable by the element surface S2 of the ultrasound probe 300, $|\Theta| < 90°$ are performed (step S100).

Then, by the processes from the steps S90 to S100, among receiving time data $D_n$ (n=1, 2, ...) obtained at each emission angle $\Theta$, receiving time data $D_n$ with the ultrasound reaching position (receiving position) X" being closest to the position of the element (ultrasound transducer 302) on the element surface S2 (for example, with an absolute value of a difference between the X coordinate of the point X" and the X coordinate of the closest element being a predetermined value or less) is extracted. Then, the extracted receiving time data $D_n$ is stored in the memory (storage unit 102) as receiving time data of the element (the ultrasound transducer 302 closest to the reaching position X" of the received wave) (step S102).

In the processing shown in FIG. 9, the receiving time data stored in step S102 is used to determine the local sound speed value in the region A (lattice point $X_{ROI}$).

In the embodiment, by superimposing the received waves from the lattice points, and the propagation time $T_{SUM}$ of the ultrasound is calculated for only a path where the received waves strengthen each other except a path where the received waves cancel each other. Specifically, acoustic ray tracing of the ultrasound reflected at the lattice point $X_{ROI}$ in the region of interest ROI in the subject OBJ is performed, and only the receiving time of the received wave directly reaching each element of the ultrasound probe 300 (or reaching the position closest to each element) is used to determine the local sound speed value at the lattice point $X_{ROI}$. According to the embodiment, the local sound speed value at the lattice point $X_{ROI}$ in the subject OBJ can be calculated in fewer processes with accuracy.

Fourth Embodiment

Next, a fourth embodiment of the present invention will be described. In the descriptions below, descriptions relating to the same configurations as in the first embodiment will be omitted.

In the embodiment, in the acoustic ray tracing in step S76 in FIG. 9, a time (receiving time) that elapses after the ultrasound transmitted from the ultrasound probe 300 to be reflected at the lattice point $X_{ROI}$ before reaching the element surface S2 of the ultrasound probe 300 is calculated for all elements $C_n$ (n=1, 2, ...) on the element surface S2.

Figure 11:
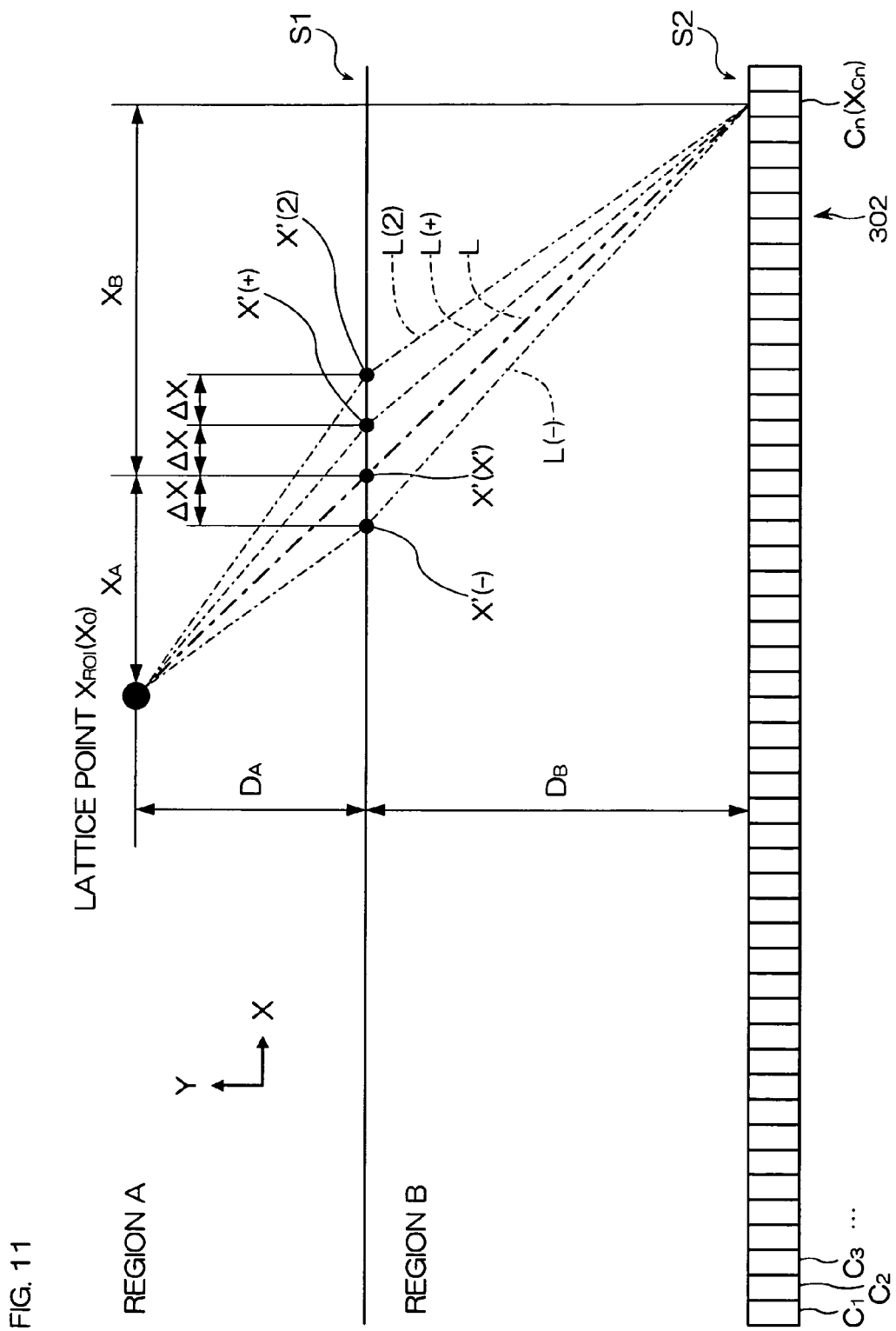
FIG. 11 schematically shows an arithmetical operation procedure of a local sound speed value in a subject according to a fourth embodiment of the present invention.

FIG. 11 schematically shows an arithmetical operation procedure of a local sound speed value in a subject according to the fourth embodiment of the present invention.

In the embodiment, first, as shown in FIG. 11, a linear acoustic ray L connecting a lattice point $X_{ROI}$ in a region of interest ROI and each element $C_n$ (n=1, 2, ...) of an ultrasound probe 300 is assumed, and a propagation time $T_R$ for the ultrasound to reach the element $C_n$ along the acoustic ray L is calculated.

Then, an intersection point X' of the acoustic ray L and a boundary surface S1 is moved in ±X directions by a predetermined amount ΔX to set acoustic rays (L(+) and L(−) respectively), and propagation times $T_{R+}$ and $T_{R-}$ for the ultrasound to reach the element $C_n$ along the acoustic rays L(+) and L(−) are calculated.

Then, the propagation time $T_R$ and the propagation times $T_{R+}$ and $T_{R-}$ are compared to determine a movement direction of the point X' for reducing the propagation time $T_R$ of the ultrasound.

Then, the same arithmetical operation is repeated for the acoustic ray (L(+) or L(−)) obtained by moving the point X' in a direction of reducing the propagation time $T_R$ to specify an acoustic ray of ultrasound from the lattice point $X_{ROI}$ to each element $C_n$ (n=1, 2, ...) of the ultrasound probe 300. Then, a receiving time $T_{SUM}$ for the ultrasound transmitted in the +Y direction from the ultrasound probe 300 to reach each element $C_n$ (n=1, 2, ...) along the acoustic ray specified by the above described process is calculated.

As described above, in the embodiment, acoustic rays for all elements $C_n$ (n=1, 2, ...) of the ultrasound probe 300 can be obtained to allow the local sound speed value to be determined with higher accuracy.

Now, an acoustic ray tracing process according to the fourth embodiment of the present invention will be described with reference to a flowchart in FIG. 12.

First, an element position $C_n$ for an arithmetical operation is set to $C_o$ (step S110). Then, the element position $C_n$ for the arithmetical operation is updated to $C_{n+1}$ (step S112).

Then, a linear acoustic ray L from the lattice point $X_{ROI}$ to the element $C_n$ of the ultrasound probe 300 is set. Then, a propagation time $T_R$ for ultrasound output from the lattice point $X_{ROI}$ to reach the element surface S2 along the acoustic ray L is calculated (step S114).

When an X coordinate of the lattice point $X_{ROI}$ is $X_0$, an X coordinate of the element $C_n$ is $X_{Cn}$, and an X coordinate of the intersection point X' of the boundary surface S1 between the regions A and B and the acoustic ray L is X', a distance $X_A$ in the X direction between the lattice point $X_{ROI}$ and the point X', and a distance $X_B$ in the X direction between the point X' and the element $C_n$ is obtained by the following expressions (12) and (13).

$$X_A = |X' - X_0| = |X_{Cn} - X_0| \times D_A/(D_A + D_B) \quad (12)$$

$$X_B = |X_{Cn} - X'| = |X_{Cn} - X_0| \times D_B/(D_A + D_B) \quad (13)$$

The propagation time $T_R$ is obtained by the following expression (14):

$$T_R = \sqrt{X_A^2 + D_A^2}/V_A + \sqrt{X_B^2 + D_B^2}/V_B \quad (14)$$

Next, a point X'(+) shifted in the +X direction from the point X' by a predetermined amount ΔX, and a point X'(−) shifted in the −X direction from the point X' by the predetermined amount ΔX are set. A propagation time $T_{R+}$ for ultrasound from the lattice point $X_{ROI}$ to reach the element $C_n$ along the acoustic ray L(+) from the lattice point $X_{ROI}$ through the point X'(+) to the element $C_n$, and a propagation time $T_{R-}$ for ultrasound from the lattice point $X_{ROI}$ to reach the element $C_n$ along the acoustic ray L(−) from the lattice point $X_{ROI}$ through the point X'(−) to the element $C_n$ are calculated.

The propagation time $T_{R+}$ is obtained by assigning $X_A = X_A + \Delta X$ and $X_B = X_B - \Delta X$ to the expression (14). The propagation time $T_{R-}$ is obtained by assigning $X_A = X_A - \Delta X$ and $X_B = X_B + \Delta X$ to the expression (14).

Then, the propagation time $T_R$ and the propagation times $T_{R+}$ and $T_{R-}$ calculated as described above are compared to determine a movement direction of the point X' for reducing the propagation time $T_R$ (step S116). In step S116, when $T_{R-} \geq T_R > T_{R+}$, the movement direction of the point X' is set in the +X direction. When $T_{R-} < T_R \leq T_{R+}$, the movement direction of the point X' is set in the −X direction.

When movements of the point X' in either of the ±X directions do not reduce the propagation time $T_R$ (that is, when $T_R \leq T_{R-}$ and $T_R \leq T_{R+}$) (Yes in step S118), a propagation time $T_{SUM}$ for the ultrasound transmitted from the element surface S2 of the ultrasound probe 300 to be reflected at the lattice point $X_{ROI}$ to reach the element $C_n$ along the acoustic ray L is calculated, and stored as receiving time data of the element $C_n$ in the memory (storage unit 102) (step S126).

In the case of No in step S118, the point X' is shifted by the predetermined amount ΔX in a direction determined to reduce the propagation time $T_R$ (hereinafter referred to as a reducing direction) (step S120). Also, a propagation time (specifically, the smaller one of $T_{R-}$ and $T_{R+}$ in step S116) for the ultrasound emitted from the lattice point $X_{ROI}$ to reach the element $C_n$ along the acoustic ray obtained by connecting the point X' shifted in step S120 and the lattice point $X_{ROI}$ and the element $C_n$ is held as a propagation time $T_R$.

Then, an acoustic ray L(2) is set obtained by connecting a point X'(2) further shifted from the point X' by ΔX in the reducing direction and the lattice point $X_{ROI}$ and the element $C_n$. Then, a propagation time $T_R'$ for the ultrasound emitted from the lattice point $X_{ROI}$ to reach the element $C_n$ along the acoustic ray L(2) is calculated (step S122). In the example shown in FIG. 8, the +X direction is assumed as the reducing direction.

Then, the propagation time $T_R'$ and the propagation time $T_R$ held in step S120 are compared (step S124). When $T_R' < T_R$ (Yes in step S124), the process returns to step S120.

When $T_R' \geq T_R$ (No in step S124), a time $T_{SUM}$ for the ultrasound transmitted from the ultrasound probe 300 to be reflected at the lattice point $X_{ROI}$ to reach the element $C_n$ along the acoustic ray set in step S120 is calculated, and stored as receiving time data of the element $C_n$ in the memory (storage unit 102) (step S126).

As the processes in steps S112 to S128 are repeated, and the arithmetical operations for all the elements $C_n$ (n=1, 2, ...) on the ultrasound probe 300 are performed.

A position of a reaching position $X_c$ on the element surface S2 when the point X' is moved is calculated, and X' and $X_C$ closest to an element position to be obtained may be used.

Fifth Embodiment

Next, a fifth embodiment of the present invention will be described. In the descriptions below, descriptions relating to the same configurations as in the first embodiment will be omitted.

Figure 10:
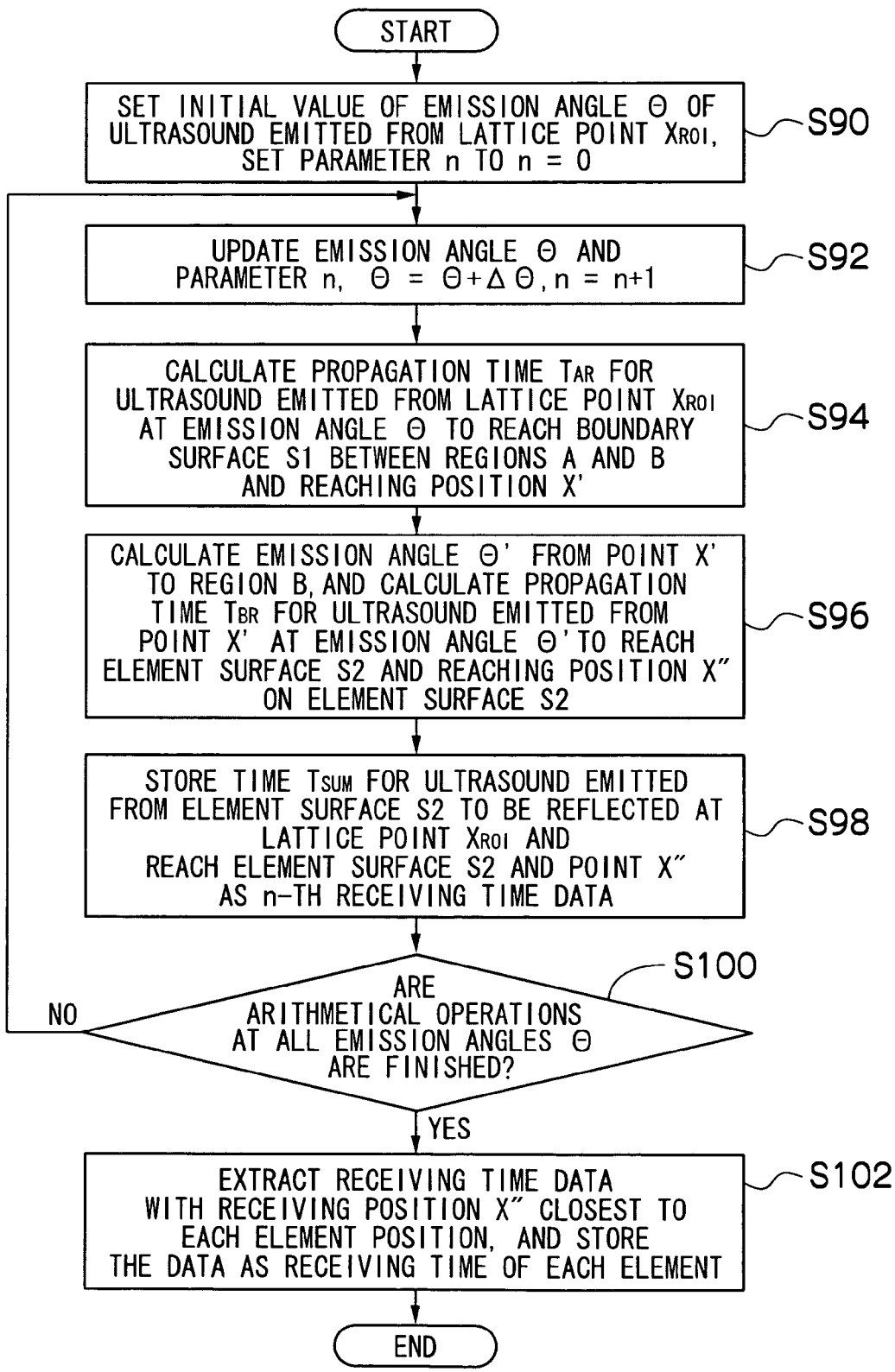
FIG. 10 is a flowchart showing a calculation process of a receiving time of a received wave by acoustic ray tracing according to the third embodiment of the present invention.
Figure 12:
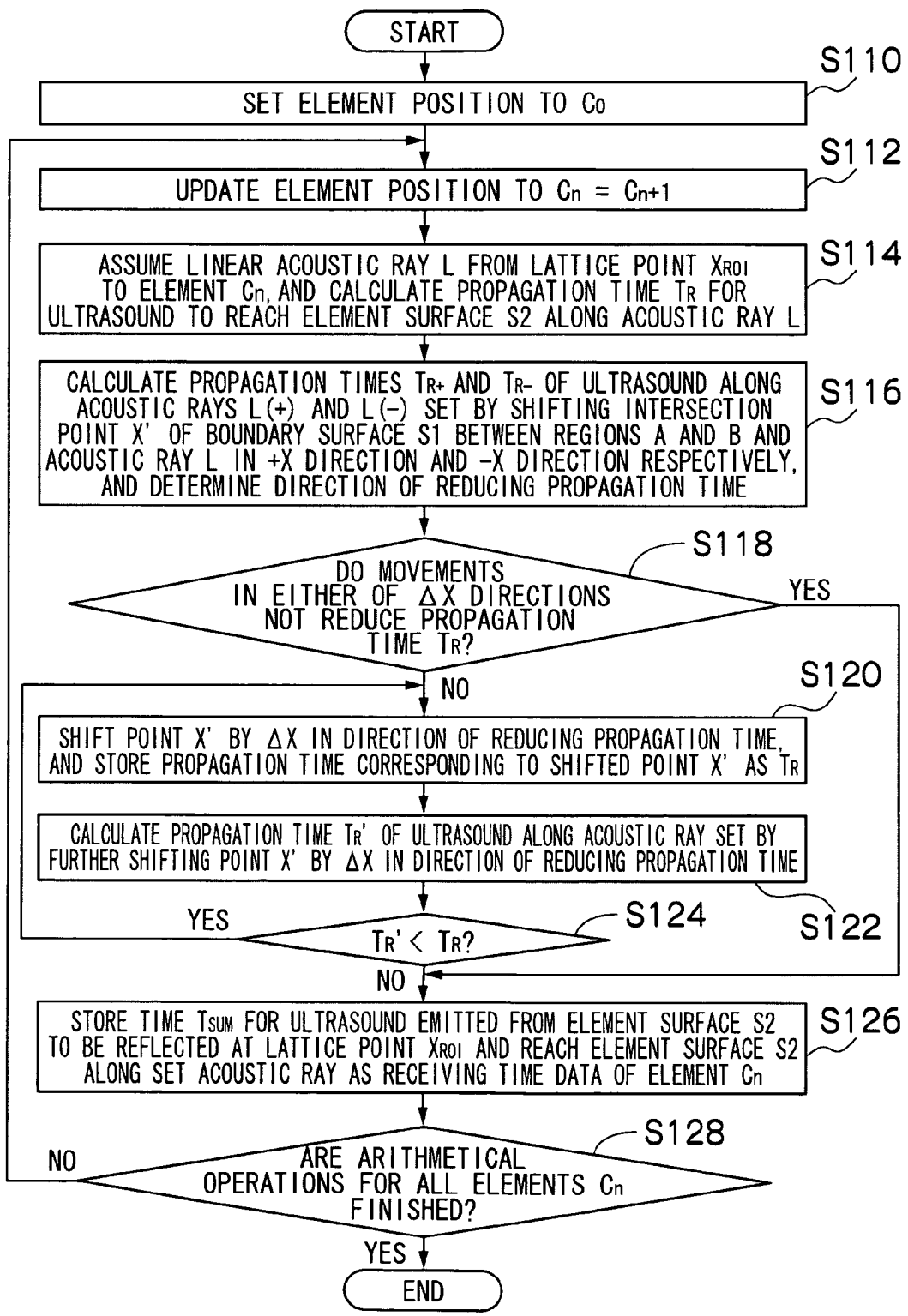
FIG. 12 is a flowchart showing a calculation process of a receiving time of a received wave by acoustic ray tracing according to the fourth embodiment of the present invention.

In the embodiment, the receiving time data obtained by the method shown in FIG. 10 or 12 is used as a delay curve, and an arithmetical operation process of a local sound speed value is performed in order from a lattice point in a shallow layer to obtain a local sound speed value in a desired region of interest in a subject OBJ (see FIG. 5).

Figure 13:
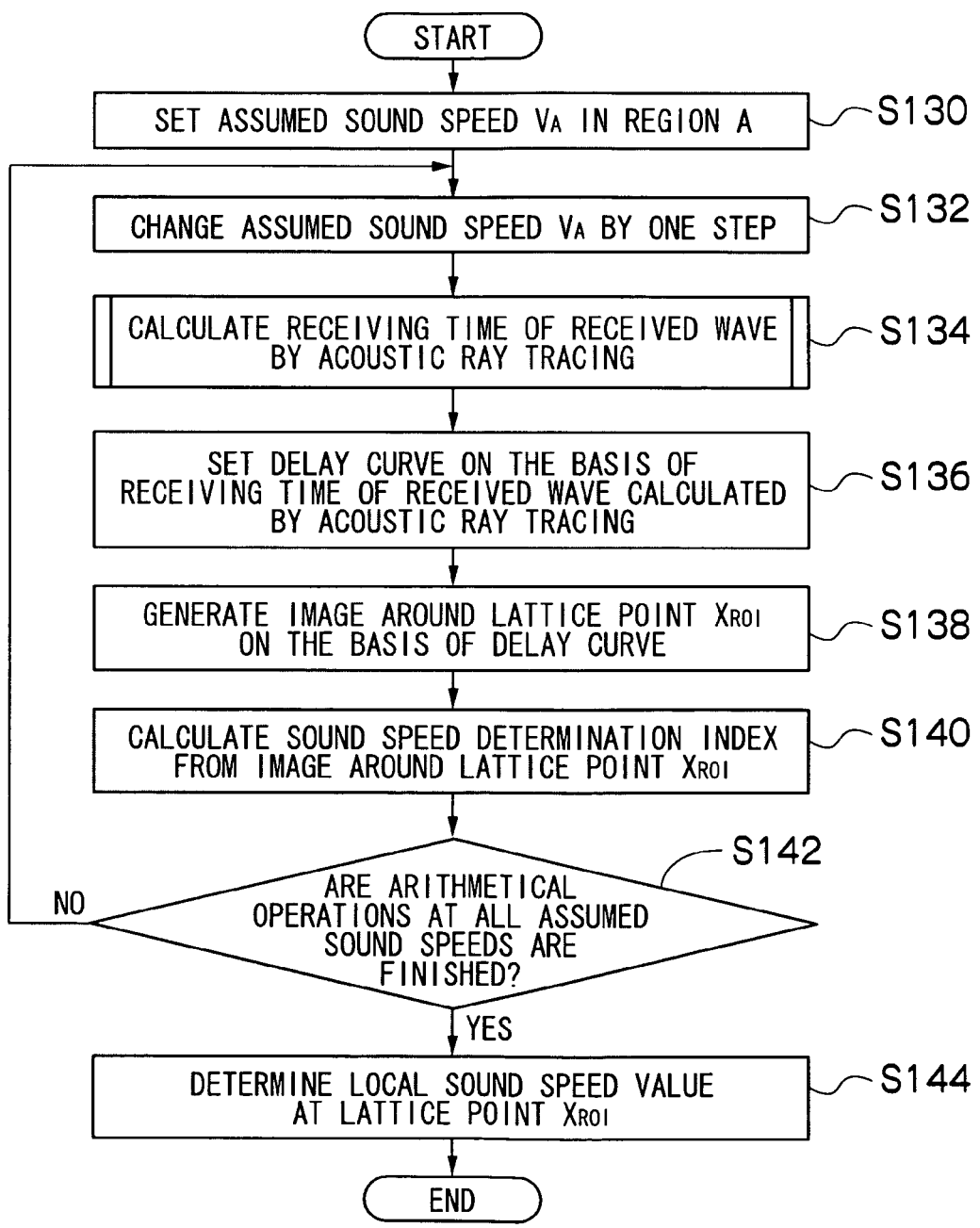
FIG. 13 is a flowchart showing an arithmetical operation process of the local sound speed value according to a fifth embodiment of the present invention.
Figure 14B:
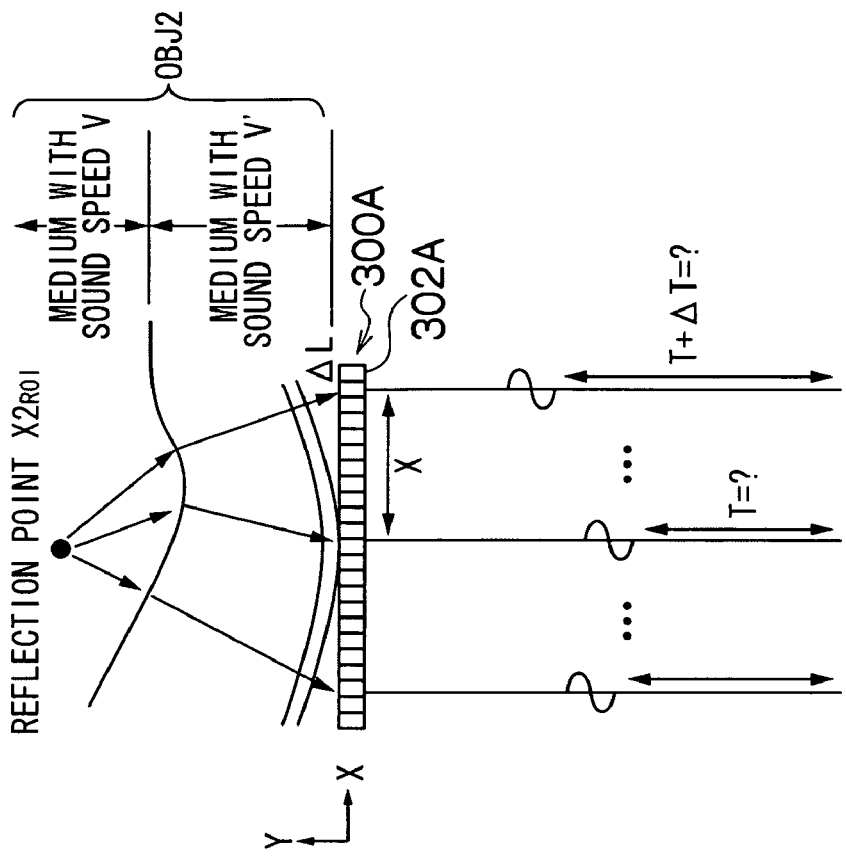
FIGS. 14A and 14B schematically show an arithmetical operation process of a local sound speed value.
Figure 14A:
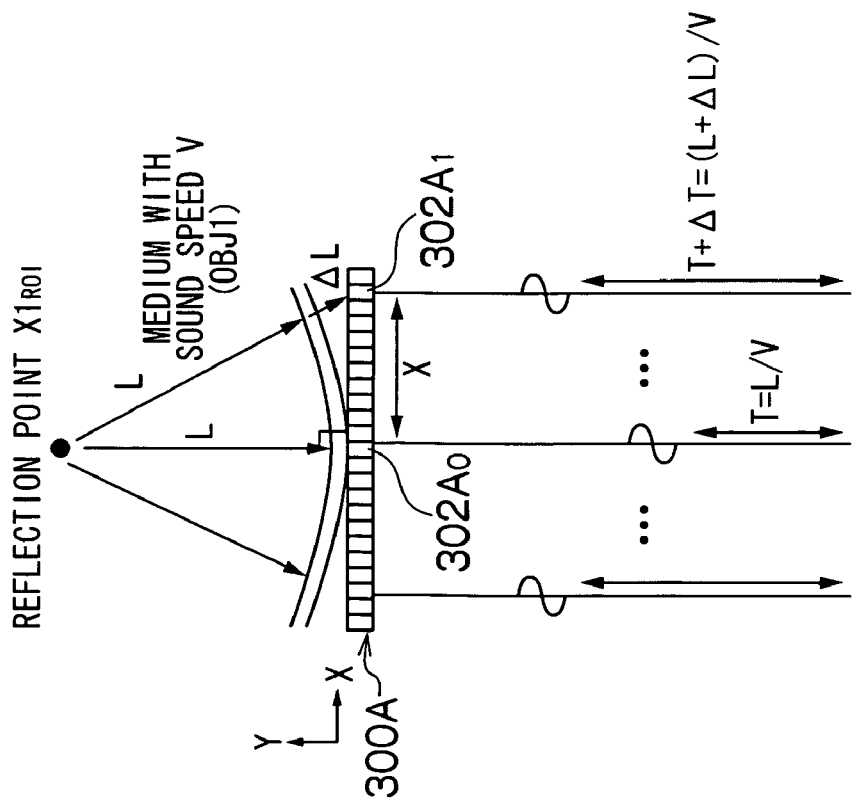

FIG. 13 is a flowchart showing the arithmetical operation process of the local sound speed value in the subject according to the fifth embodiment of the present invention.

In the embodiment, the arithmetical operation process of the local sound speed value is performed in order from the lattice point in the shallow layer. In the arithmetical operation of the local sound speed value, to determine a local sound speed value at a lattice point $X_{ROI}$, a received wave from a lattice point in a shallower depth than the lattice point $X_{ROI}$ is required. Thus, in order to determine local sound speed values at lattice points ($A1_N, A2_N, \ldots$) in a depth N, received waves from all lattice points ($A1_{N-1}, A2_{N-1} \ldots$) in a depth (N−1) are held in a memory (storage unit 102). After the processing of all lattice points in the depth N is finished, the received waves in the depth (N−1) are abandoned, and received waves from all lattice points in the depth N are held instead.

Optimum sound speed values (environmental sound speeds) at lattice points $A1_0, A2_0, \ldots$ in the shallowest layer are obtained on the basis of received waves received from the lattice points $A1_0, A2_0, \ldots$ set in the subject OBJ.

A range of lattice points (a region where the lattice points $A1_0, A2_0, \ldots, A1_1, A2_1, \ldots, A1_N, A2_N, \ldots$ are arranged) and an interval between the lattice points in XY directions used in the arithmetical operation of the local sound speed value are previously determined as in the first embodiment. Multiple times of determination of the local sound speed value may be performed using lattice points with a different interval and in a different range.

Next, as shown in FIG. 13, an initial value $V_A$ of an assumed sound speed at the lattice point $X_{ROI}$ is set (step S130). Then, the assumed sound speed is changed by one step (step S132), and on the basis of the assumed sound speed $V_A$ and the environmental sound speed (that is, the environmental sound speed in the shallowest layer) $V_B$, acoustic ray tracing of a received wave reflected at the lattice point $X_{ROI}$ and reaching the ultrasound transducer 302 is performed to calculate the a receiving time of the received wave (step S134). The acoustic ray tracing process in step S134 is the same as the embodiment shown in FIG. 10 or 12.

A delay curve around the lattice point $X_{ROI}$ is set from the receiving time of the received wave obtained in step S134 (step S136).

Then, an ultrasound image (B mode image) around the lattice point $X_{ROI}$ is generated on the basis of the delay curve (step S138), and a sound speed determination index is calculated from the image around the lattice point $X_{ROI}$ (step S140). The sound speed determination index is an index for determining a sound speed obtained on the basis of at least one of contrast of the image, a space frequency of the image in a scanning direction, and dispersion of the space frequency. Calculation of the sound speed determination index may be performed after image generation at all assumed sound speeds (after step S142).

Then, steps S132 to S142 are repeated, and when arithmetical operations at all assumed sound speed values are finished (Yes in step S142), a local sound speed value at the lattice point $X_{ROI}$ is determined on the basis of the sound speed determination index (step S144).

Then, the processing shown in FIG. 13 is repeated in order from the shallowest layer, and local sound speed values at lattice points ($A1_1, A2_1, \ldots, A1_2, A2_2, \ldots, A1_N, A2_N, \ldots$) in a deeper layer are successively obtained to calculate a local sound speed value in the desired region of interest ROI (lattice point $X_{ROI}$) in the subject OBJ.

According to the embodiment, the acoustic ray tracing is repeated in order from the shallow layer in the subject OBJ to determine the local sound speed value, thereby allowing the local sound speed value in the subject OBJ to be determined with high accuracy.

In the embodiments, the lattice points are arranged in the XY directions at regular intervals, but may be arranged at non-regular intervals so that the lattice points are arranged on a boundary between regions with a substantially uniform sound speed. The region with a substantially uniform sound speed is considered to be a substantially identical region with uniform brightness in an amplitude image, and thus the lattice points may be arranged along a boundary where average brightness changes by a threshold or more. High brightness is obtained in a tissue boundary with different acoustic impedances, and thus the lattice points may be arranged along a place with higher brightness than other places by a threshold or more. Further, an edge (of brightness of the B mode image) is detected by a differentiation filter or the like, and the lattice points may be set along the edge. Further, a user can set the arrangement of the boundary between the regions A and B and the lattice points on the boundary using a pointing device 204 or the like while watching the B mode image.

The embodiments may be applied to a case where the ultrasound transducers are two-dimensionally arranged, or the ultrasound transducers are arranged in any curved shape rather than a planar shape.

Also, at least one of a transmitting focus process and a receiving focus process may be performed according to the optimum sound speed, the received waveform, or the delay curve of each region (each lattice point) obtained in the embodiments to reconstruct the B mode image.

In the embodiments, a threshold for setting the lattice points may be adjusted so that the number of lattice points per unit area is a predetermined number or more, or the lattice points are laterally arranged at a predetermined density or more.

In the embodiment, when the environmental sound speeds at the lattice points A1, A2, . . . and the lattice point $X_{ROI}$ are obtained, or when the local sound speed at the lattice point $X_{ROI}$ is obtained based on the received waves from the lattice points A1, A2, . . . , the received waves are not determined on the basis of only the environmental sound speeds or the local sound speeds, but correlation of ultrasound detection signals detected by adjacent elements may be taken, and contrast and sharpness may be determined to determine the received waves by adjusting a delay. This provides a smooth waveform of the received wave and increases accuracy of sound speed determination.

In the environmental sound speed determination process or the local sound speed determination process, the transmitting focus may be changed in addition to the receiving focus process. Not only that a delay is obtained based on an assumed resultant received wave determined by a local sound speed value assumed for the lattice point $X_{ROI}$, the receiving focus is performed according to the delay; or the receiving focus is performed according to the delay determined by the environmental sound speed assumed for the lattice point $X_{ROI}$; but also that the transmitting focus is performed to allow an increase in determination accuracy of a sound speed. For example, a delay added at transmitting timing of ultrasound from each element in actual transmission of ultrasound to the lattice point $X_{ROI}$ may be changed, or an assumed transmission delay in aperture synthesis of an ultrasound beam (transmission wave) may be changed.

What is claimed is:

1. An ultrasound diagnostic apparatus comprising:
   an ultrasound probe including a plurality of ultrasound transducers configured to transmit ultrasound to a subject and configured to receive the ultrasound reflected by the subject to output an ultrasound detection signal;
   an optimum sound speed value determination device configured to determine an optimum sound speed value in a region of interest in the subject and optimum sound speed values at lattice points set in a region between the region of interest in the subject and the ultrasound probe on the basis of the ultrasound detection signal;
   a first arithmetical operation device configured to calculate a first received wave received from the region of interest on the basis of the optimum sound speed value in the region of interest when the ultrasound is transmitted to the region of interest;

a second arithmetical operation device configured to set an assumed sound speed in the region of interest, and configured to calculate a second received wave received from the region of interest on the basis of the assumed sound speed and the optimum sound speed value at the lattice points when the ultrasound is transmitted from the ultrasound probe to the region of interest; and a local sound speed value determination device configured to make a determination of a local sound speed value in the region of interest on the basis of the first received wave and the second received wave.

2. The ultrasound diagnostic apparatus according to claim 1, wherein the local sound speed value determination device determines that the local sound speed value in the region of interest is the assumed sound speed used for a calculation of the second received wave at which a difference between the first received wave and the second received wave is minimized.

3. An ultrasound diagnostic apparatus comprising:

an ultrasound probe including a plurality of ultrasound transducers configured to transmit ultrasound to a subject and configured to receive the ultrasound reflected by the subject to output an ultrasound detection signal;

an arithmetical operation device configured to set an assumed sound speed in a certain region of interest in the subject, and configured to calculate a received wave received from the region of interest when ultrasound is transmitted from the ultrasound probe to the region of interest, wherein the received wave is calculated on the basis of the assumed sound speed and received waves received from lattice points set in a region between the region of interest and the ultrasound probe;

a sound speed determination index arithmetical operation device configured to obtain a delay on the basis of the received wave received from the region of interest to generate an image in the region of interest on the basis of the delay, and configured to calculate a sound speed determination index on the basis of the image; and a local sound speed value determination device configured to make a determination of a local sound speed value in the subject on the basis of the sound speed determination index.

4. The ultrasound diagnostic apparatus according to claim 3, wherein the sound speed determination index arithmetical operation device calculates the sound speed determination index on the basis of at least one of contrast of the image, a space frequency of the image in a scanning direction, and dispersion of the space frequency.

5. The ultrasound diagnostic apparatus according to claim 1, further comprising a lattice point setting device configured to set a lattice point on a boundary between regions with a substantially uniform sound speed in the subject.

6. The ultrasound diagnostic apparatus according to claim 3, further comprising a lattice point setting device configured to set a lattice point on a boundary between regions with a substantially uniform sound speed in the subject.

7. The ultrasound diagnostic apparatus according to claim 1, further comprising an amplitude image generation device configured to perform at least one of a transmitting focus process and a receiving focus process on the basis of the determination result of the local sound speed value in the subject to generate an amplitude image indicating an amplitude of the received wave with brightness of a point.

8. The ultrasound diagnostic apparatus according to claim 1, further comprising a display device configured to display the determination result of the local sound speed value.

9. The ultrasound diagnostic apparatus according to claim 8, further comprising an amplitude image generation device configured to generate an amplitude image indicating an amplitude of the received wave with brightness of a point on the basis of the ultrasound detection signal, wherein the display device displays the determination result of the local sound speed value so as to be superimposed on the amplitude image or placed with the amplitude image side by side.

10. The ultrasound diagnostic apparatus according to claim 8, further comprising an amplitude image generation device configured to generate an amplitude image indicating an amplitude of the ultrasonic echo with brightness of a point on the basis of the ultrasound detection signal, wherein the display device displays the determination result of the local sound speed value by changing brightness or color of the amplitude image.

11. The ultrasound diagnostic apparatus according to claim 9, further comprising a display mode switching device configured to switch a display mode between a first display mode in which the amplitude image is displayed alone and a second display mode in which the determination result of the local sound speed value in the subject is displayed.

12. An ultrasound diagnostic method comprising:

providing an ultrasound probe including a plurality of ultrasound transducers configured to transmit ultrasound to a subject and configured to receive the ultrasound reflected by the subject to output an ultrasound detection signal;

an optimum sound speed value determination step of determining an optimum sound speed value in a region of interest in the subject and optimum sound speed values at lattice points set in a region between the region of interest in the subject and the ultrasound probe on the basis of the ultrasound detection signal obtained by the ultrasound probe;

a first arithmetical operation step of calculating a first received wave received from the region of interest on the basis of the optimum sound speed value in the region of interest when the ultrasound is transmitted to the region of interest;

a second arithmetical operation step of setting an assumed sound speed in the region of interest, and calculating a second received wave received from the region of interest on the basis of the assumed sound speed and the optimum sound speed value at the lattice points when the ultrasound is transmitted from the ultrasound probe to the region of interest; and a localسound speed value determination step of making a determination of a local sound speed value in the region of interest on the basis of the first received wave and the second received wave.

13. An ultrasound diagnostic method comprising:

providing an ultrasound probe including a plurality of ultrasound transducers configured to transmit ultrasound to a subject and configured to receive the ultrasound reflected by the subject;

an arithmetical operation step of setting an assumedسound speed in a certain region of interest in the subject, and calculating a received wave received from the region of interest when ultrasound is transmitted from the ultrasound probe to the region of interest, wherein the received wave is calculated on the basis of the assumed sound speed and received waves received from lattice points set in a region between the region of interest and the ultrasound probe;

a sound speed determination index arithmetical operation step of obtaining a delay on the basis of the received wave received from the region of interest to generate an image in the region of interest on the basis of the delay, and calculating a sound speed determination index on the basis of the image; and a local sound speed value determination step of making a determination of the local sound speed value in the subject on the basis of the sound speed determination index.

14. The ultrasound diagnostic apparatus according to claim 2, wherein the difference is calculated by taking cross-correlation between the first and second received waves, and one of delaying the first received wave by a delay obtained based on the second received wave to perform phase matching addition of the waves, or delaying the second received wave by a delay obtained based on the first received wave to perform phase matching addition of the waves.

15. The ultrasound diagnostic method according to claim 12, wherein it is determined that the local sound speed value in the region of interest is the assumed sound speed used for a calculation of a received wave at which a difference between the first received wave and the second received wave is minimized in the local sound speed value determination step.

16. The ultrasound diagnostic method according to claim 15, wherein the difference is calculated by taking cross-correlation between the first and second received waves, one of delaying the first received wave by a delay obtained based on the second received wave to perform phase matching addition of the waves, or delaying the second received wave by a delay obtained based on the first received wave to perform phase matching addition of the waves.

17. The ultrasound diagnostic method according to claim 13, wherein the sound speed determination index is calculated on the basis of at least one of contrast of the image, a space frequency of the image in a scanning direction, and dispersion of the space frequency, in the sound speed determination index arithmetical operation step.

18. The ultrasound diagnostic apparatus according to claim 1, wherein the optimum sound speed value is a sound speed value with a highest sharpness of an image.

19. The ultrasound diagnostic method according to claim 12, wherein the optimum sound speed value is a sound speed value with a highest sharpness of an image.

\* \* \* \* \*